US012138016B2

(12) United States Patent
Hocking

(10) Patent No.: US 12,138,016 B2
(45) Date of Patent: Nov. 12, 2024

(54) METHOD TO QUANTIFY THE HEMODYNAMIC AND VASCULAR PROPERTIES IN VIVO FROM ARTERIAL WAVEFORM MEASUREMENTS

(71) Applicant: Grant Hocking, Alpharetta, GA (US)

(72) Inventor: Grant Hocking, Alpharetta, GA (US)

(*) Notice: Subject to any disclaimer, the term of this patent is extended or adjusted under 35 U.S.C. 154(b) by 659 days.

(21) Appl. No.: 17/343,067

(22) Filed: Jun. 9, 2021

(65) Prior Publication Data
US 2021/0386299 A1    Dec. 16, 2021

Related U.S. Application Data

(60) Provisional application No. 63/039,524, filed on Jun. 16, 2020.

(51) Int. Cl.
A61B 5/1455    (2006.01)
A61B 5/00      (2006.01)
(Continued)

(52) U.S. Cl.
CPC ...... *A61B 5/02007* (2013.01); *A61B 5/02035* (2013.01); *A61B 5/02116* (2013.01);
(Continued)

(58) Field of Classification Search
CPC .............. A61B 5/1455; A61B 5/02007; A61B 5/02035; A61B 5/02116
See application file for complete search history.

(56) References Cited

U.S. PATENT DOCUMENTS

2002/0038090 A1    3/2002 Sunagawa et al.
2003/0135124 A1    7/2003 Russell
(Continued)

FOREIGN PATENT DOCUMENTS

WO    WO2019217778    11/2019
WO    WO20190217778   11/2019
WO    WO20200150455    7/2020

OTHER PUBLICATIONS

International Search Report/Written Opinion released in corresponding International Patent Application No. PCT/US2021/036592 on Sep. 27, 2021; 10 pages.
(Continued)

*Primary Examiner* — Marjan Fardanesh
(74) *Attorney, Agent, or Firm* — Smith Gambrell & Russell LLP

(57) ABSTRACT

Disclosed herein are in vivo non-invasive methods and devices for the measurement of the hemodynamic parameters, such as such as blood pressure, stroke volume, cardiac output, performance of the aortic and mistral heart valves, arterial blood velocity profile, blood viscosity and the blood flow induced arterial wall shear stress, hypertensive/hypotensive and vasodilation/vasocontraction state and aging status of a subject, and the mechanical anelastic in vivo properties of the arterial blood vessels. An exemplary method requires obtaining the peripheral pulse volume waveform (PVW), the peripheral pulse pressure waveform (PPW), and the peripheral pulse velocity waveform (PUW) from the same artery; calculating the time phase shift between the PPW and PVW, and the plot of pulse pressure versus pulse volume; and determining the blood pressures and power law components of the anelastic model from the waveforms PPW and PVW, the cardiac output and heart valves performances from the waveforms PPW and PUW, and the anelastic in vivo properties of the descending, thoracic and abdominal aorta. The disclosed methods and devices can be used to diagnose and treat cardiovascular disease in a subject in need thereof.

31 Claims, 20 Drawing Sheets

(51) Int. Cl.
*A61B 5/02* (2006.01)
*A61B 5/021* (2006.01)
*A61B 5/0265* (2006.01)
*A61B 5/0285* (2006.01)
*A61B 5/029* (2006.01)
*A61B 8/06* (2006.01)

(52) U.S. Cl.
CPC .......... *A61B 5/0265* (2013.01); *A61B 5/0285* (2013.01); *A61B 5/029* (2013.01); *A61B 5/14552* (2013.01); *A61B 5/4839* (2013.01); *A61B 5/6843* (2013.01); *A61B 5/7278* (2013.01); *A61B 8/06* (2013.01)

(56) References Cited

U.S. PATENT DOCUMENTS

| | | |
|---|---|---|
| 2004/0158162 A1 | 8/2004 | Narimatsu |
| 2004/0249292 A1 | 12/2004 | Davis et al. |
| 2019/0069842 A1 | 3/2019 | Rothberg et al. |

OTHER PUBLICATIONS

Nabeel, P.M., et al., "Local Pulse Wave Velocity: Theory, Methods, Advancements and Clinical Applications", IEEE Reviews in Biomedical Engineering, IEEE vol. 12, Jul. 26, 2019; 39 pages.
Extended European Search Report released by the European Patent Office on Jun. 17, 2024 for corresponding European Patent Application No. 21825702.0; 8 pages.

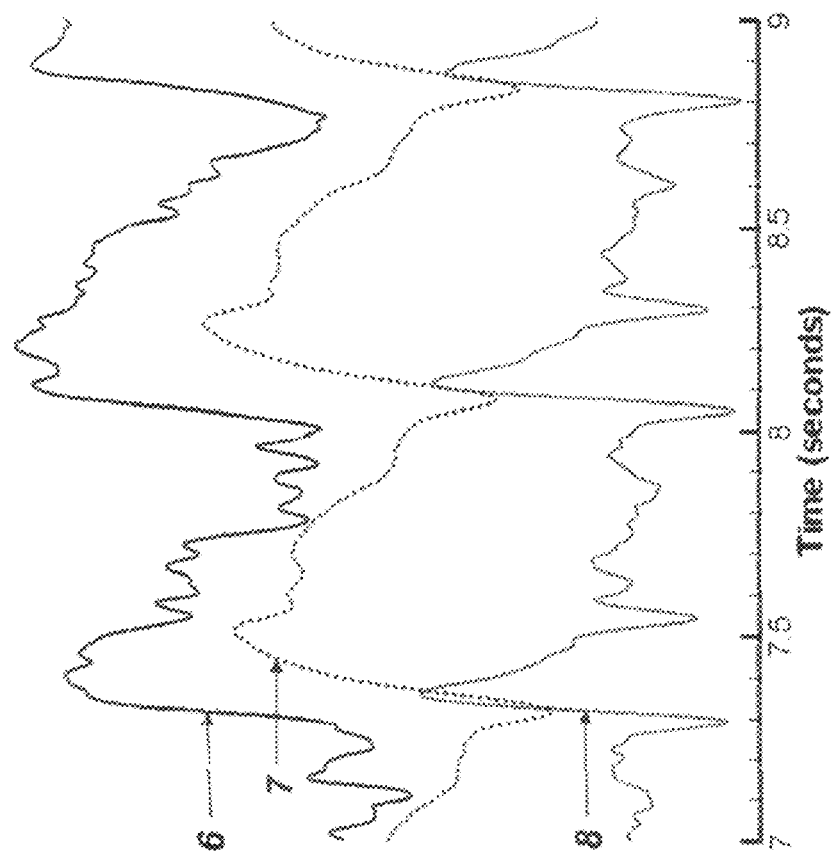
FIG. 1A
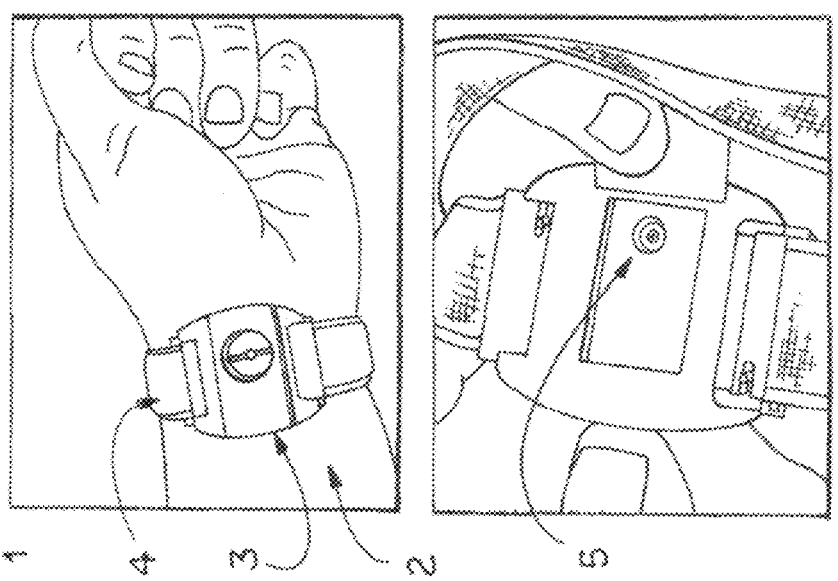
FIG. 1B
FIG. 1C

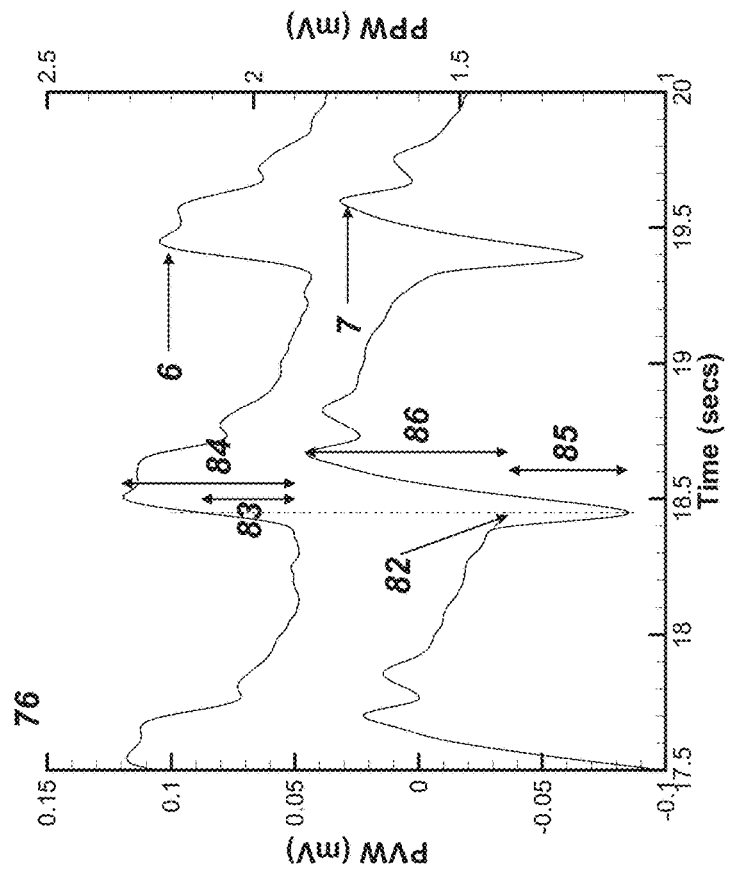
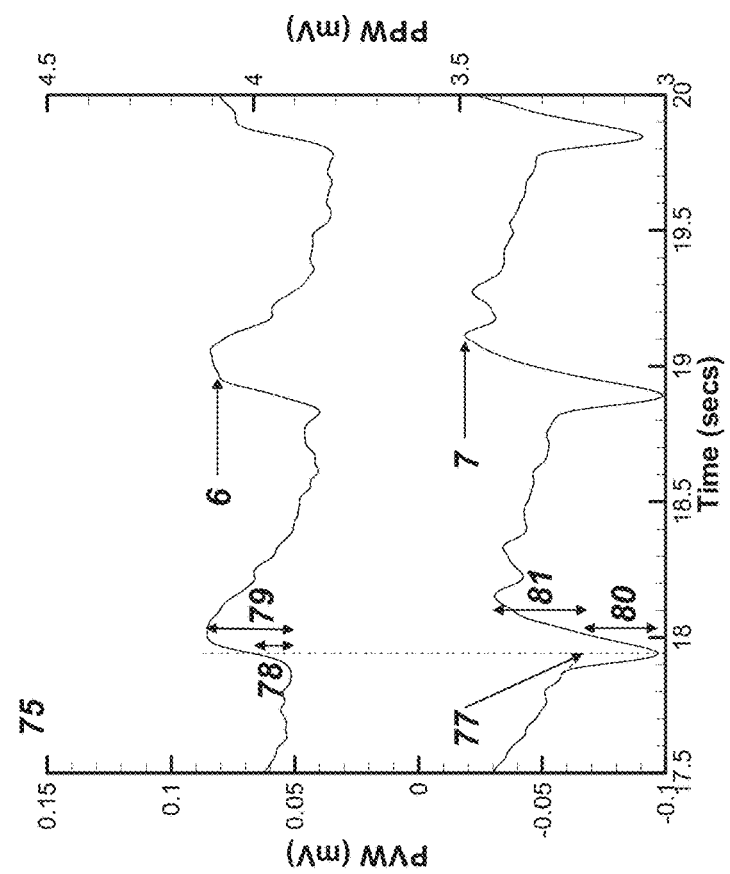
FIG. 14A
FIG. 14B

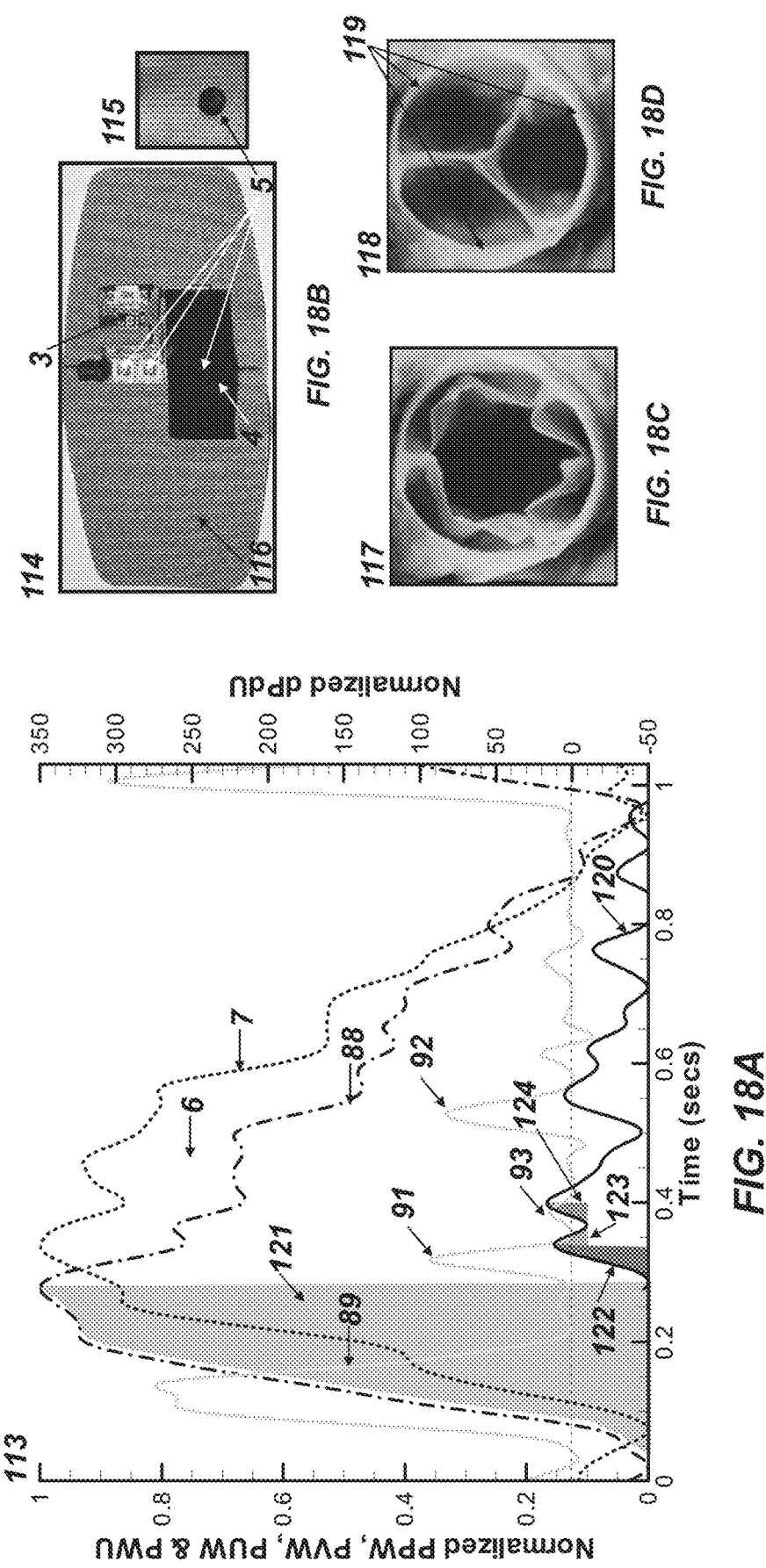

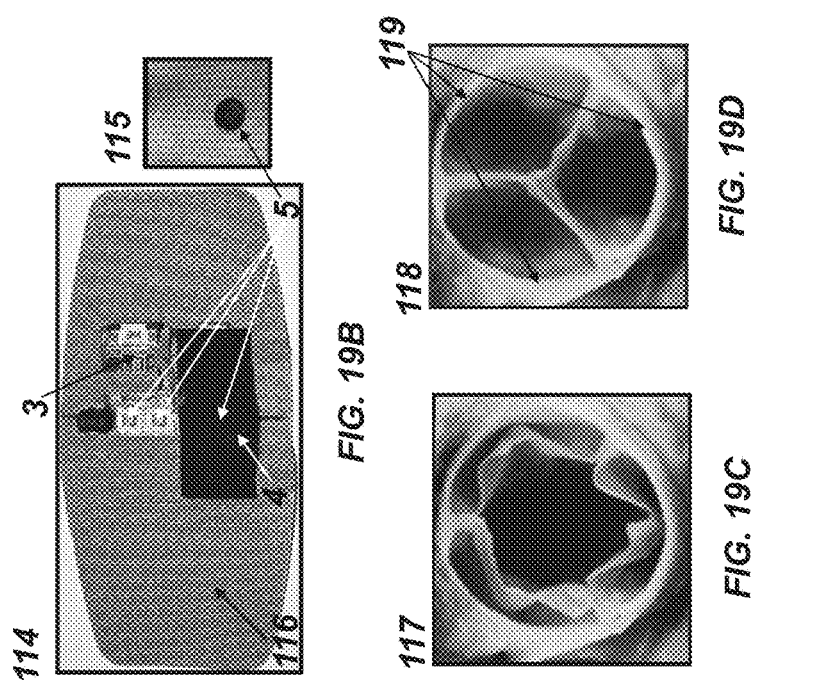
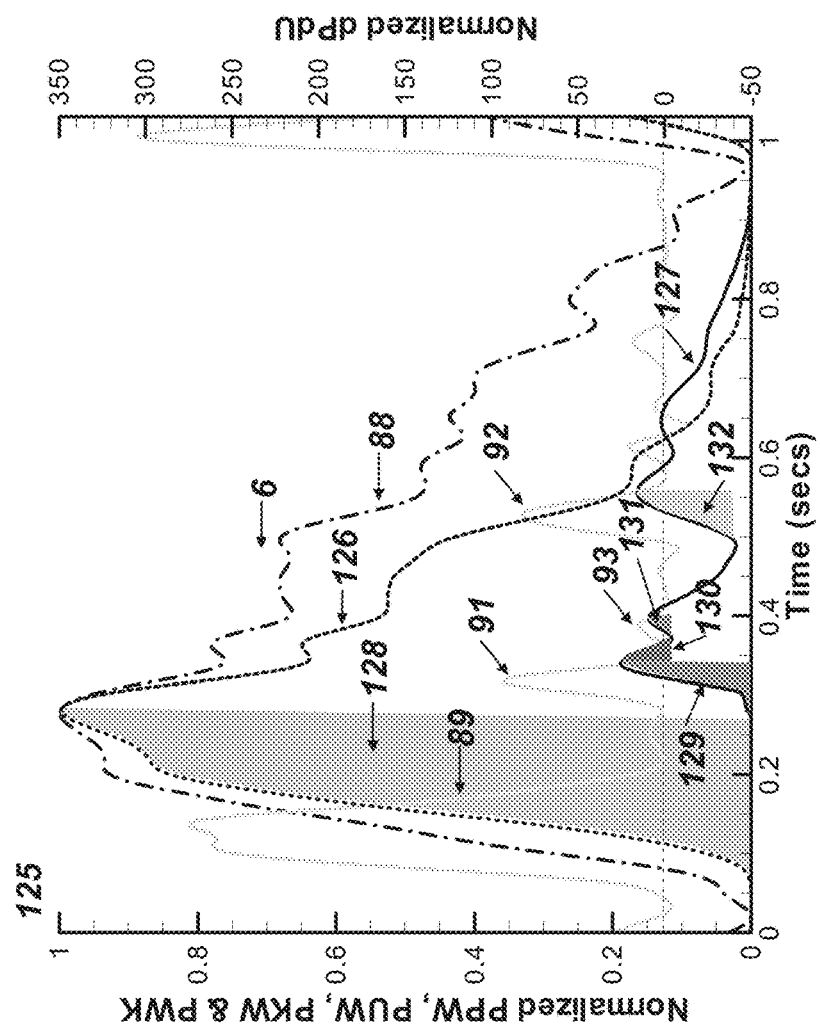
FIG. 19A
FIG. 19B
FIG. 19C
FIG. 19D

METHOD TO QUANTIFY THE HEMODYNAMIC AND VASCULAR PROPERTIES IN VIVO FROM ARTERIAL WAVEFORM MEASUREMENTS

CLAIM OF PRIORITY

This application claims priority from U.S. Provisional Patent Application Ser. No. 63/039,524, filed Jun. 16, 2020, which is incorporated herein in its entirety.

FIELD OF THE INVENTION

The present invention generally relates to the quantification of the hemodynamic parameters and hypertension status of a living subject. More specifically, the present invention relates to systems and methods of using sensed peripheral arterial pulse waveform measurements to assess hemodynamic parameters, such as blood pressure, stroke volume, cardiac output, performance of the aortic and mistral heart valves, arterial blood velocity profile, blood viscosity and the induced arterial wall shear stress, hypertensive/hypotensive state, vasodilation/vasocontraction state, and also to quantify the mechanical anelastic properties of the blood vessels in vivo.

BACKGROUND OF THE INVENTION

Conventional methods of establishing the hypertensive state of a subject involves blood pressure measurements, and depending on the state of the subject's hypertension, medication may be prescribed to lower the subject's blood pressure. The effectiveness of such medication is monitored by blood pressure measurements. Provided the medication lowers the subject's blood pressure to acceptable levels, then it is presumed that the medication is considered effective in controlling the subject's hypertension. The impacts that the prescribed medication have on the subject in general, and in particular the subject's blood vessels are unknown.

In subjects experiencing angina pectoris, glyceryl trinitrate may be prescribed as a vasodilator to inhibit the onset of angina pectoris during exercise. The effectiveness of the medication on specific subjects is basically trial and error. During vasodilation, the blood vessels change their properties significantly, and without diagnostic measurements of these changes, the impact of the medication, and its potential impact on the subject's blood vessels is not known. Angina can also be due to narrowed or blocked arteries around the heart, ischemia, emotional stress, exposure to very hot or cold temperatures, heavy meals and smoking.

The changes to the arterial vascular vessels mechanical properties due to hypertension, aging, diabetes, mellitus, arteriosclerosis, hypercholesterolemia and ischemic heart disease are difficult to quantify using current measurement techniques such as simple pulse wave velocity (PWV) measurements, electrocardiogram (EKG) and blood pressure measurements. The anelastic in vivo properties of the peripheral arterial blood vessels and their hypertrophy can provide valuable insight into these processes on a subject's wellbeing, and the impact of medication to treat such disorders and their associated changes to the subject's arterial vascular vessel properties. The acute effect of vasoconstriction and vasodilation with resulting increase and decrease in blood pressure, have significant impact on the anelastic response of the body's peripheral arterial vascular vessels. In vivo quantification of these anelastic changes are essential in diagnosing the issues relating to aging and disease, and also as important, the impact of medication on changes to the peripheral arterial blood vessels' anelastic properties and their hypertrophy.

Arteries stiffen progressively with age and disease, even in the earliest stages of arteriosclerosis, prior to any clinical manifestation and anatomical evidence of the disease. In vivo quantification of minor changes in the peripheral artery blood vessels properties would provide an extremely useful clinical tool for the assessment of cardiovascular risk, from arterial vessel stiffening, plaque buildup, arteriosclerosis and/or elevated risk of aneurysm or dissection. PWV and augmentation index are associated with cardiovascular burden, but do not have the sensitivity necessary to detect minor changes in the hemodynamic parameters, such as cardiac output and the mechanical properties of the peripheral arterial blood vessels nor their hypertrophy. Alternative methods for such an assessment are urgently needed.

Therefore, it is an object of the invention to provide non-invasive systems and methods for the measurement of the hemodynamic parameters and mechanical anelastic properties of the arterial blood vessels in a subject.

SUMMARY OF THE INVENTION

The present invention is an in vivo non-invasive method and apparatus for the measurement of the hemodynamic parameters, such as blood pressure, stroke volume, cardiac output, performance of the aortic and mistral heart valves, arterial blood velocity profile, blood viscosity and the blood flow induced arterial wall shear stress, hypertensive/hypotensive and vasodilation/vasocontraction state and aging status of a subject, and the mechanical anelastic in vivo properties of the arterial blood vessels. The method requires measuring the peripheral pulse volume waveform (PVW), using an infra-red emitter and sensor positioned over an artery, and a force sensor positioned over the same artery measuring the peripheral pulse pressure waveform (PPW), and a velocity sensor positioned over the same artery measuring the peripheral pulse velocity waveform (PUW), with all sensors contained in a wristband, that applies a slight force and being of adequate compliance, for the force sensor to measure the arterial pulse pressure waveform (PPW) as a tonometer, and a strap tension actuator to modify the strap band tension. The time phase shift between the PPW and PVW, and the plot of pulse pressure versus pulse volume, quantifies the anelastic properties of the peripheral arterial blood vessels in vivo, and the subject's hypertensive state including hypertrophy. The wrist strap applied at two different tensions allows the patient's systolic and diastolic blood pressures to be measured, and the full mechanical anelastic properties of the peripheral arterial blood vessels in vivo can be determined; such as the pulse shear strain at systolic, the secant shear modulus, the anelastic power law constants, and the hypertensive state of the patient, including hypertrophy.

From the quantified subject's systolic and diastolic blood pressures, the full mechanical anelastic properties of the peripheral arterial blood vessels in vivo can be determined, such as the pulse shear strain at systolic, the shear modulus, and the anelastic power law constants, during both the systolic and diastolic phases experienced by the arterial blood vessels over a cardiac cycle. From the time location of the second forward pulse wave in the PVW, the form of the hypertension of the subject can be quantified.

The change in the peripheral arterial blood vessels anelastic and hemodynamic parameters, including blood pressure, stroke volume, cardiac output during vasodilation or vasocontraction, either from induced hypotension/hypertension, physical exercise, breathing exercises or induced by medication or illness, are quantified from the measured waveforms PPW, PVW and PUW. These changes in the arterial blood vessel hemodynamic and anelastic properties, quantify the extent of vasodilation, vasocontraction, loss of stroke volume, induced hypertension/hypotension and possible onset of cardiogenic shock. The determination of the anelastic blood vessel properties provides a direct measure of whether such vasodilation is sufficient in improving the tone of the subject's peripheral artery blood vessels, and thus reverse or slow the rate of change of the subject's hypertensive state. Historical recording of a subject's vasodilation/vasocontraction on arterial blood vessel anelastic properties, is able to determine with considerably greater accuracy than current procedures, the impact of any prescribed medication, diet or exercise program on the subject's hypertensive state.

Other objects, features and advantages of the present invention will become apparent upon reviewing the following description of the preferred embodiments of the invention, when taken in conjunction with the drawings and the claims.

BRIEF DESCRIPTION OF THE DRAWINGS

FIG. 1A is an exemplary plot that can be obtained using processing device 3. Waveform 6 is the peripheral arterial pulse pressure waveform (PPW), waveform 7 is the arterial pulse volume waveform (PVW), and waveform 8 is the first time derivate of PVW.

FIG. 1B is a view of the arm of the subject, 2, with a processing device 3 held in place by a strap 4.

FIG. 1C shows the back of the device 3 with a reflective pulse optical plethysmograph, force sensor and velocity sensors and tension actuator 5 for positioning over the subject's radial artery, with all sensors connected to the device 3.

FIG. 14A is the time history of the peripheral pulse pressure waveform (PPW), and the pulse volume waveform (PVW), recorded from the optical plethysmograph and the force sensor positioned over the radial artery, at a low strap tension.

FIG. 14B is the time history of the peripheral pulse pressure waveform (PPW), and the pulse volume waveform (PVW), recorded from the optical plethysmograph and the force sensor positioned over the radial artery, at a high strap tension.

FIG. 18A is the time history of the peripheral pulse pressure waveform (PPW), volume waveform (PVW) and velocity waveform (PUW), recorded from an optical plethysmograph, the force and velocity sensors positioned over the carotid artery, and the calculated wave intensity analysis (dPdU) waveform constructed from the waveforms PPW and PUW.

FIG. 18B shows a processing device 3 held in place by a flexible fabric adhesive containing a reflective pulse optical plethysmograph, force and velocity sensors 5 for positioning over a subject's carotid artery, with all sensors connected to the device 3.

FIG. 18C shows the aortic valve in an open position.

FIG. 18D shows the aortic valve in a closed position.

FIG. 19A is the time history of the peripheral pulse pressure waveform (PPW), volume waveform (PVW) and velocity waveform (PUW), recorded from an optical plethysmograph, the force and velocity sensors positioned over the carotid artery, the calculated wave intensity analysis (dPdU) waveform and the calculated pulse power waveform (PKW), both constructed from the waveforms PPW and PUW.

FIG. 19B shows a processing device 3 held in place by a flexible fabric adhesive containing a reflective pulse optical plethysmograph, force and velocity sensors 5 for positioning over a subject's radial artery, with all sensors connected to the device 3.

FIG. 19C shows the aortic valve in an open position.

FIG. 19D shows the aortic valve in a closed position.

DETAILED DESCRIPTION OF THE PREFERRED EMBODIMENT

Figure 2:
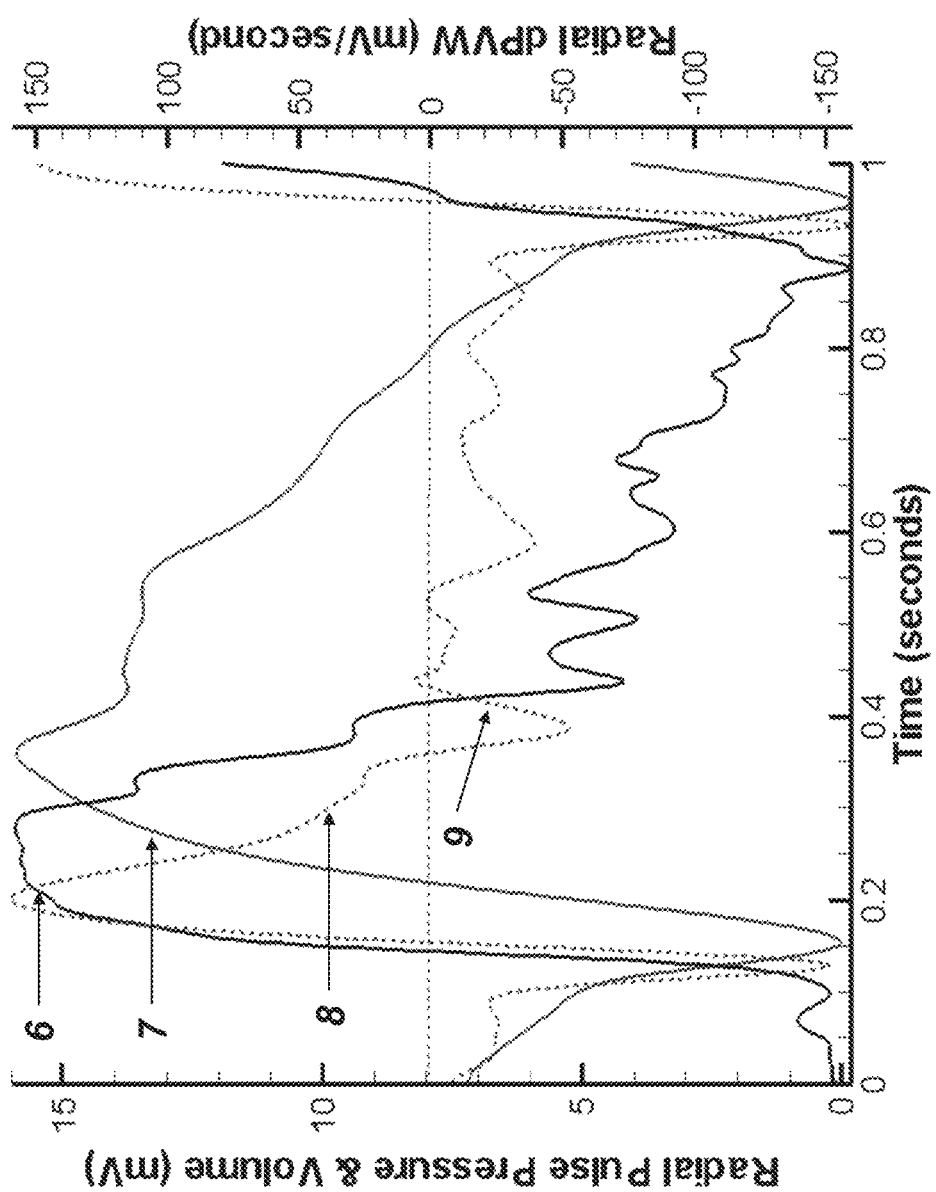
FIG. 2 is the time history of the peripheral pulse volume and pulse pressure waveforms PVW and PPW, recorded from an optical plethysmograph and force sensor positioned over the radial artery, showing the out of phase of the two waveforms, due to the anelasticity of the artery blood vessels, and the time history of the constructed first time derivative of the PVW.

Disclosed herein is an in vivo, non-invasive method and apparatus for the measurement of hemodynamic parameters and mechanical anelastic in vivo properties of the arterial blood vessels in a subject. The current standard method of measuring a patient's blood pressure is by a cuff over the upper arm, and the entire arm is occluded, which can be distressing to many patients especially if their blood pressures are elevated. The apparatus and methods disclosed herein are a significant improvement over current practice, since it determines the patient's blood pressure and other hemodynamic properties from two wrist band tensions applied over an artery. From the measured systolic and diastolic blood pressures, the non-linear anelastic material properties of peripheral arterial blood vessels can be determined from pulse pressure and pulse volume waveform measurements, and from these waveforms, the hypertensive state, hypertrophy and mechanical anelastic in vivo properties of the peripheral arterial blood vessels can be quantified. Additional details of the apparatus and methods are described below.

Representatively illustrated in FIG. 1A is a system 1 and associated method which embody exemplary components of the disclosed apparatus. FIG. 1B shows the arm of the subject 2 with a processing device 3 held in place by a strap 4. As shown in FIG. 1C, device 3 contains a sensor suite 5 which can include any variation of the following sensors: a reflective pulse optical plethysmograph sensor, force sensors, velocity sensors, skin temperature sensor, barometric pressure sensor and strap tension actuator. The sensors and the strap tension actuator can be connected to the device 3, or can be contained within the device 3.

The device 3 can be designed to be positioned over an arterial vessel in a subject. In one embodiment, the arterial vessel can be the radial artery, brachial artery, axillary artery, carotid artery, femoral artery, or tibial artery. In a preferred embodiment, the device is designed as a wristband to be positioned over the radial artery.

Plethysmography is a method that is used to estimate the skin blood flow using infrared light. Traditionally, it is used to measure oxygen saturation, blood pressure, and cardiac output. Optical plethysmographs use an infrared light sent into the tissue and the amount of the backscattered light corresponds with the variation of the blood volume. In one embodiment, the pulse optical plethysmograph sensor within the disclosed device is an infrared optical plethysmograph sensor, a visible light plethysmograph sensor, or a pulse oximetry sensor.

The force sensor could be of either a resistive, strain gage, piezoelectric, capacitance or mems type. The velocity sensor could be either a Hall sensor with an applied magnetic field either from a permanent magnet or an electrical activated electromagnet or an ultrasound Doppler sensor to measure the arterial pulse velocity waveform (PUW).

The disclosed processing device 3 can also contain a motion sensor in the sensor suite 5. In such an embodiment, the motion sensor acts to ensure accurate results by only collecting and processing the waveforms PPW, PVW and PUW when the motion sensor is within certain threshold limits. The motion sensor can be either of the piezoelectric, accelerometer or mems type.

The disclosed processing device 3 can also contain a strap tension actuator. The strap tension actuator can be electrical, hydraulic, pneumatic, mechanical or manually actuated, and be of the piezoelectric, electromechanical, stepper motor, geared or spring type. In one embodiment, the applied strap tension from the actuator results in a normal skin pressure of from about 10 mmHg to about 50 mmHg over the artery.

Methods of using the disclosed processing device are disclosed herein. The current disclosure further improves upon previously disclosed methods by obtaining non-invasive measurements of peripheral pulse volume waveform (PVW) and peripheral pulse pressure waveform (PPW) and using the measurements to determine hemodynamic parameters and mechanistic anelastic properties of arterial blood vessels in a subject. The hemodynamic parameters and mechanistic anelastic properties can then be used to diagnose disease, determine the efficacy of drug treatments, monitor patients having pneumonia, cardiac disorders, sepsis, asthma, obstructive sleep apnea, hypopnea, anesthesia, pain, or narcotic use, or other means in which close, real time monitoring of cardiac function are necessary.

In one embodiment, the peripheral pulse volume waveform (PVW) measurement is obtained using an infra-red emitter and sensor positioned over an artery. The peripheral pulse pressure waveform (PPW) is obtained by a force sensor positioned over the same artery. The peripheral pulse velocity waveform (PUW) is obtained by a velocity sensor positioned over the same artery All of the aforementioned sensors are contained in the disclosed wristband device that applies an appropriate amount of strap tension such that the device act as a tonometer. A force sensor is also included in the device to act as a tonometer and measure the arterial pulse pressure waveform (PPW).

The waveforms PPW, PVW and PUW can be transformed by either a Fast Fourier Transform FFT or the power spectral density method to determine the respiratory and heart rates and associated higher frequencies. The time phase shift between the PPW and PVW, and the plot of pulse pressure versus pulse volume, quantifies the anelastic properties of the peripheral arterial blood vessels in vivo. By applying two strap tensions over a patient's artery with the actuator, the patient's systolic and diastolic blood pressure are measured, and the full mechanical anelastic properties of the peripheral arterial blood vessels in vivo can be determined, such as the pulse shear strain at systolic, the secant shear modulus, the anelastic power law constants, the hypertensive/hypotensive and vasodilation/vasocontraction state of the patient, including hypertrophy. When placed over a subject's carotid artery, the device can also be used to quantify the heart stroke volume, cardiac output, aortic and mitral valves' conformance and compliance, blood velocity, viscosity and arterial wall shear stress, and the descending aorta PWV, Quality factor, secant modulus and anelastic properties.

From known values of the subject's systolic and diastolic blood pressure, the full mechanical anelastic properties of the peripheral arterial blood vessels in vivo can be determined, such as the pulse shear strain at systolic, the shear modulus, and the anelastic power law constants, during both the pressurizing and depressurizing phases experienced by the arterial blood vessels. From the time location of the second forward pulse wave in the PVW, the form of the hypertension of the subject can be determined.

The change in the peripheral arterial blood pressures and blood vessels anelastic properties during vasodilation or vasocontraction, either from induced hypotension/hypertension, physical exercise, breathing exercises or induced by medication, are quantified from the measured waveforms. These changes in the arterial blood vessel anelastic properties, quantify the extent of vasodilation, vasocontraction or induced hypertension, and provide a direct measure of whether such vasodilation is sufficient in improving the tone of the subject's peripheral artery blood vessels, and thus reverse or slow the rate of change of the subject's hypertensive state. Historical recoding of a subject's vasodilation/ vasocontraction on arterial blood vessel anelastic properties enable to determine with considerably greater accuracy than current procedures, the impact of any prescribed medication, diet or exercise program on the subject's hemodynamic parameters, such as hypertensive state, cardiac output and in vivo anelastic arterial vessel properties FIG. 2 depicts the two measured waveforms, the PPW 6, the PVW 7 and its first time derivative dPVW 8, with the prime reflected forward wave shown as 9 on the waveform dPVW. The measurements were obtained using the wristband device disclosed herein. The applied pressure of the housing over the artery is greater than 10 mmHg and less than 50 mmHg.

Figure 3:
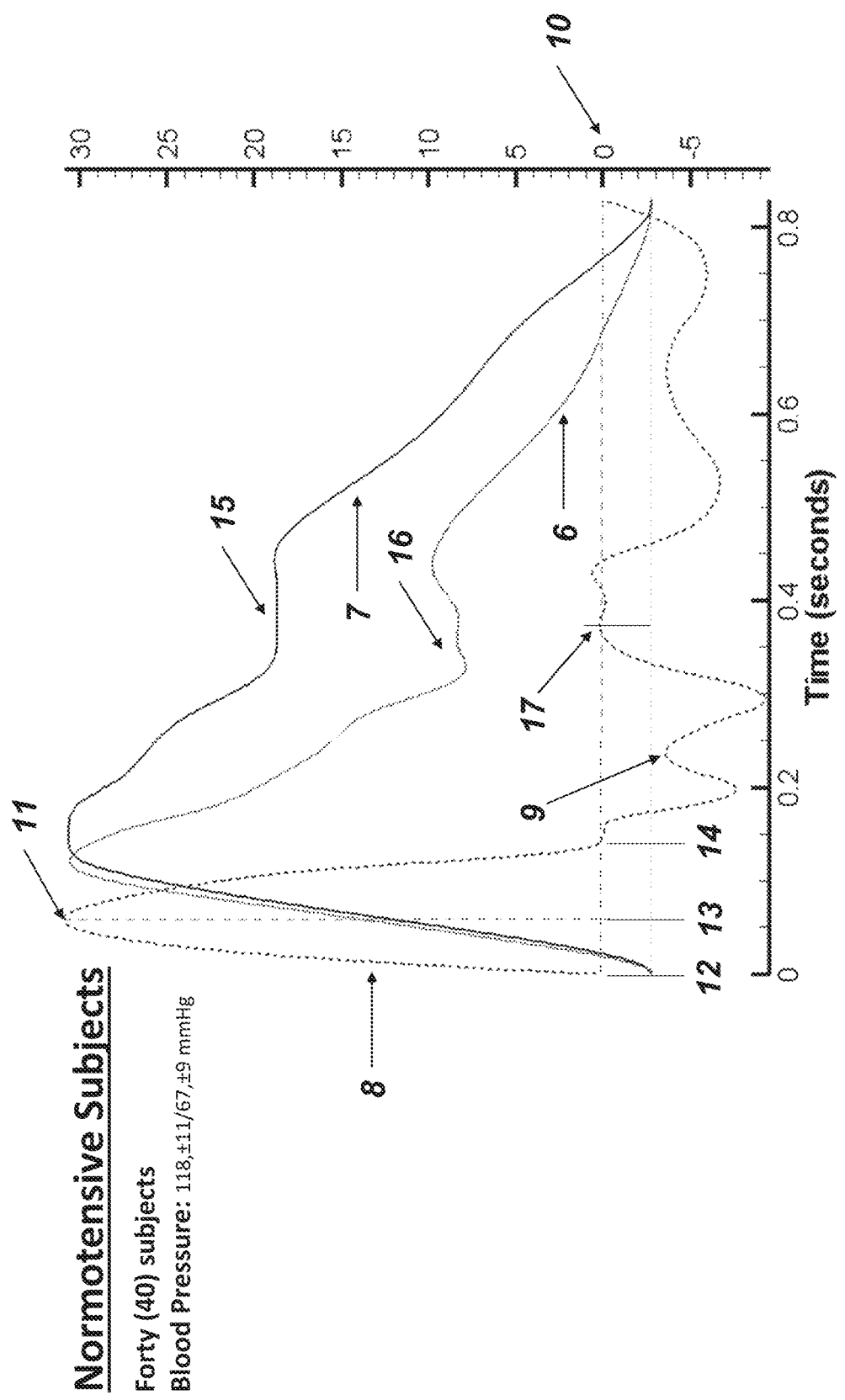
FIG. 3 is the averaged time history for forty (40) normotensive subjects of the peripheral pulse optical plethysmograph waveform (PVW) recorded from an optical plethysmograph sensor positioned over a finger, and the time history of the constructed first time derivative of the PVW, and the averaged time history of the peripheral arterial pulse pressure waveform (PPW) recorded over the radial artery.

FIG. 3 depicts the peripheral arterial pulse optical plethysmograph waveform (PVW) 7 for the averaged normalized one heart cycle time history for forty (40) normotensive subjects, recorded from an optical plethysmograph sensor positioned over a finger. Also shown is the time history of the constructed first time derivative of the PVW being the dPVW, denoted as 8, with the prime reflected forward wave shown as 9 on the waveform dPVW, and the averaged normalized time history of the peripheral arterial pulse pressure waveform (PPW) recorded over the radial artery by applanation tonometry by a piezo-resistive cantilever transducer. The PPW was time shifted to be in-phase with the PVW, as denoted by 6. The measured waveforms, Millasseau et al., 2000, were normalized prior to being averaged for the forty (40) healthy normotensive subjects, aged from 24 to 80 years. All forty of the subjects had no previous history of hypertension or cardiovascular disease, and all were normotensive (office blood pressure <140/90 mm Hg), prior to the time of the study. Blood pressure measurements during the study were (mean, ±standard deviation) 118, ±11/67, ±9 mmHg. The zero ordinate of the constructed waveform dPVW is shown as 10. The first pulse wave peak is denoted as 11. The rise and fall time intervals of the first pulse wave are given by the difference in the time abscissa of points denoted as 12, 13 and 14. With the points, being the intersection of the zero ordinate 10 and the constructed waveform dPVW, point 12 being the start of the rise of the first pulse wave, point 13 being the maximum of the first pulse wave, and point 14 being the end of the fall of the first pulse wave.

The ratio of the fall time to the rise time of the first pulse wave for the normotensive subjects as determined from points 12, 13 and 14 is 1.8. The rise and fall times of the first and subsequent pulse waves are important and highly dependent on the peripheral arterial blood vessel mechanical anelastic properties. The pulse is a soliton and as such maintains its shape virtually unattenuated provided the energy lost by anelasticity is equivalent to the loss due to dispersion. When these losses are equal, the pulse wave travels as a soliton with no change in shape until it interacts with another forward or backward traveling pulse wave, and upon separation of the two interacting soliton waves, the waves have the same shape to that before the interaction, and there is only a time shift to distinguished that the two waves have undergone an interaction. The solution of the interaction of two solitons is not linear, and so requires a non-linear approach to differentiation between the various pulse waveform. If the energy lost by anelasticity of the peripheral blood vessels deviates from a Quality factor (defined later in equation (2)) of Q=3, then the shape (fall and rise times) of the first pulse wave will change, and it is this change that can be directly correlated to the peripheral arterial blood vessel anelastic properties. The second forward pulse wave is shown as 15 on the pulse volume waveform PVW, 7, and is also shown as 16 on the measured pulse pressure waveform, 6. The second forward pulse wave, which causes closure of the aortic valve, is shown as 17 on the waveform dPVW, and its peak arrival time position in the heat beat cycle is 0.37 seconds.

Figure 4:
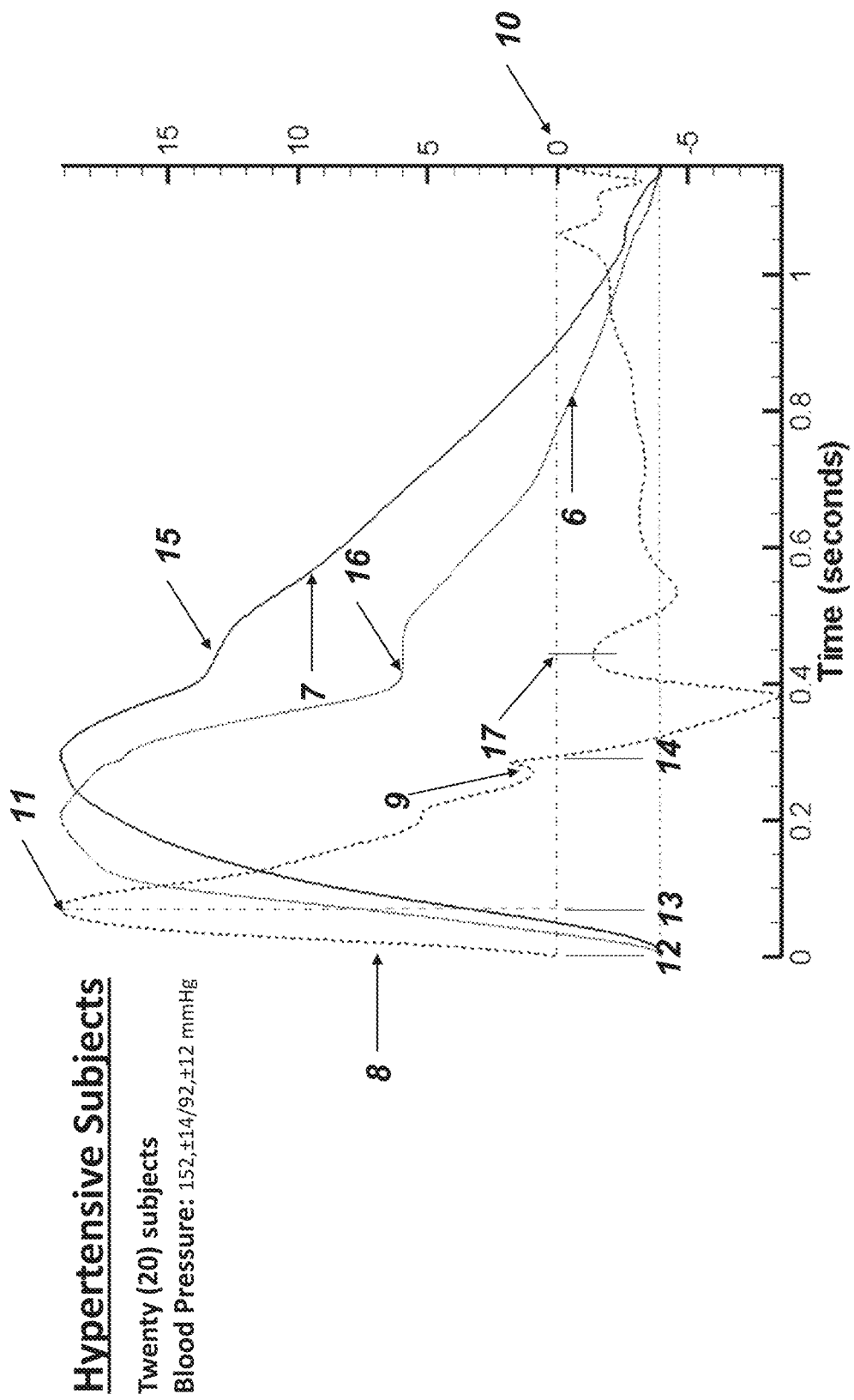
FIG. 4 is the averaged time history for twenty (20) hypertensive subjects of the peripheral pulse optical plethysmograph waveform (PVW) recorded from an optical plethysmograph sensor positioned over a finger, and the time history of the constructed first time derivative of the PVW, and the averaged time history of the peripheral arterial pulse pressure waveform (PPW) recorded over the radial artery.

FIG. 4 depicts the peripheral pulse optical plethysmograph waveform (PVW) 7 for the averaged normalized one heart cycle time history for twenty (20) hypertensive subjects, recorded from an optical plethysmograph sensor positioned over a finger. Also shown is the time history of the constructed first time derivative of the PVW being the dPVW, denoted as 8, with the prime reflected forward wave shown as 9 on the waveform dPVW. The averaged normalized time history of the peripheral arterial pulse pressure waveform (PPW) denoted as 9 was recorded over the radial artery by applanation tonometry by a piezo-resistive cantilever transducer, and was time shifted to be in-phase with the PVW, as denoted by 6. The measured waveforms, Millasseau et al., 2000, were normalized prior to being averaged for the twenty (20) hypertensive subjects, aged from 24 to 80 years. Hypertension was diagnosed on the basis of >3 measurements of office blood pressure >140/90 mm Hg, with each measurement separated by at least a week. None of the hypertensive subjects had clinical evidence of cardiovascular disease other than hypertension. Twelve (12) of the subjects were receiving antihypertensive therapy at the time of the study, (diuretics, 7 of 12; β-adrenoreceptor antagonists, 5 of 12; α-adrenoreceptor antagonists, 1 of 12; ACE inhibitors, 3 of 12; angiotensin II receptor antagonists, 2 of 12; and calcium channel blockers, 4 of 12). Blood pressure at the time of the study for the hypertensive subjects was 152, +14/92±12 mm Hg. The zero ordinate of the constructed waveform dPVW is shown as 10. The first pulse wave peak is denoted as 11. The rise and fall time intervals of the first pulse wave are given by the difference in the time abscissa of points denoted as 12, 13 and 14, with the points being the intersection of the zero ordinate 10 and the constructed waveform dPVW, point 12 being the start of the rise of the first pulse wave, point 13 being the maximum of the first pulse wave, and point 14 being the end of the fall of the first pulse wave.

The ratio of the fall time to the rise time of the first pulse wave for the normotensive subjects as determined from points 12, 13 and 14 is 3.4, a significant difference from the ratio determined for the normotensive subjects, which was 1.8. Normalizing the fall to rise time ratio to the normotensive subjects, the normalized fall to rise time for the hypertensive subjects is 1.9, and by construction of a Hypertensive Index (HI) from the forty (40) normotensive subjects as a HI=0, and the twenty (20) hypertensive subjects having a HI=100. Determining the fall to rise time ratio from the constructed waveform dPVW for any subject, the Hypertensive Index (HI) of that subject can be determined and its value will be equal to 0 for healthy normotensive subjects, but generally range from 0 to 100 for most subjects, and in cases of extreme hypertension can be >100. In some cases, the Hypertensive Index (HI) could be <0, for healthy subjects under extreme conditions such as exposure to temperature, altitude, and dehydration. The Hypertensive Index (HI) of a subject can be correlated to age, and as such can determine whether elevated levels of the Hypertensive Index (HI) are related to the effects of aging, or being accelerated due to the impacts of disease, life style or medication on the respective subject.

The second forward pulse wave causes closure of the aortic valve. The second forward pulse wave is shown as 15 on the pulse volume waveform PVW, 7, 16 on the measured pulse pressure waveform, 6, and as 17 on the waveform dPVW. Its peak arrival time position in the heart beat cycle is 0.45 seconds. The peak time arrival of the second forward pulse wave was 0.37 seconds for the normotensive subjects, whilst the peak time arrival for the hypersensitive subjects was 0.45 seconds. The normalized time arrival of the second forward pulse wave from the normotensive subjects to the hypertensive subjects is attributed solely to being genetically positive to hypertension, and not considered to be age related hypertension.

Alternatively, a piezoelectric sensor placed over the artery can better detect both the time location of the second forward pulse wave, and by integrating the piezoelectric sensor in the vicinity of the second forward pulse wave time location, the pulse volume change can be better determined for aged subjects or subjects suffering from arteriosclerosis, hypertension or severe skin decolorization. The rate of pulse volume change in the vicinity of the second forward pulse wave can be determined over time and raise alerts if this time rate of change of pulse volume starts to accelerate.

Figure 5:
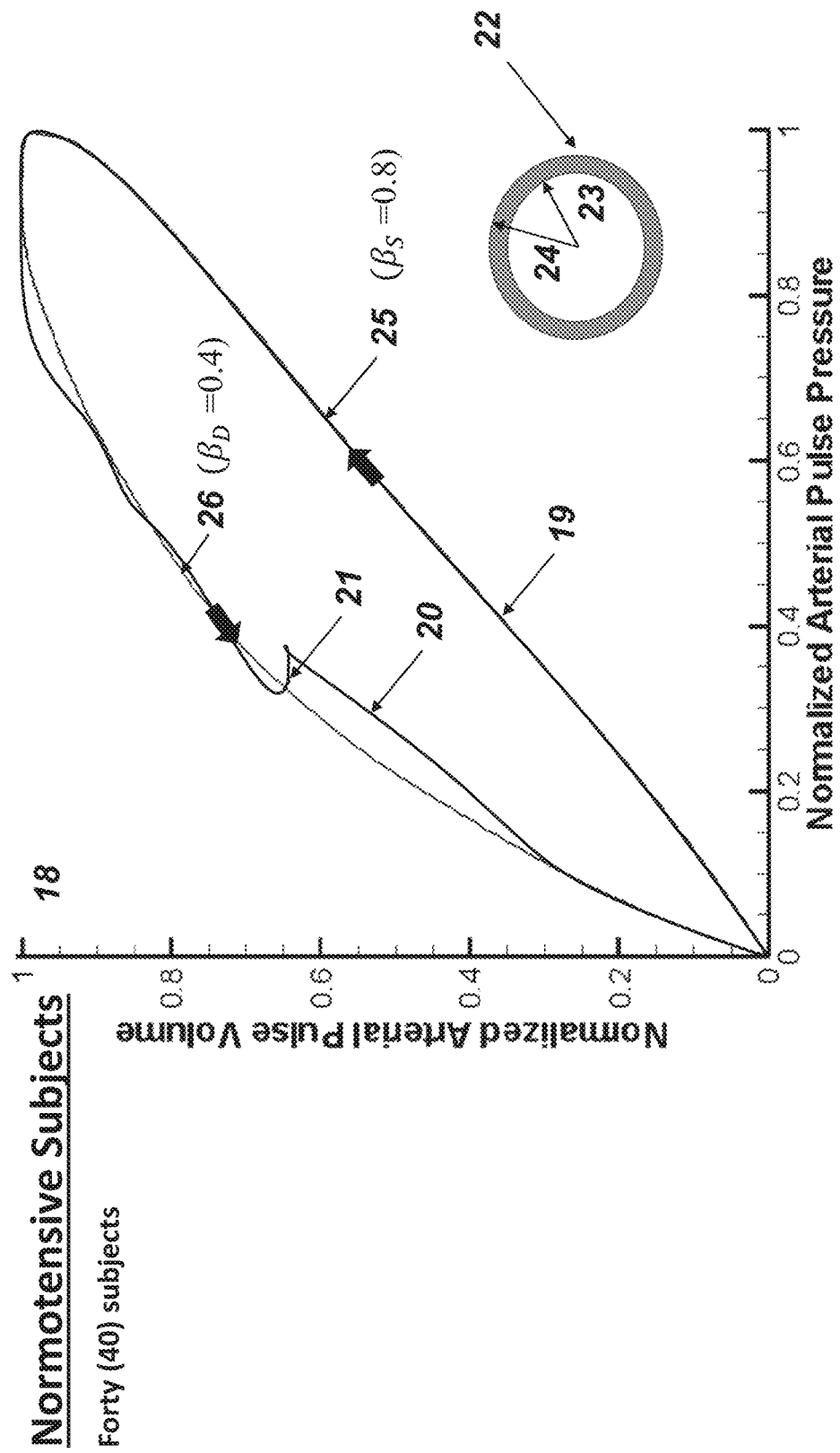
FIG. 5 is the normalized time shifted arterial pulse pressure plotted against the normalized arterial pulse volume as an average for forty (40) normotensive subjects, and the thick wall three (3) component anelastic power law model.

FIG. 5 depicts the normalized arterial pulse pressure versus normalized arterial pulse volume denoted as 18, for the forty (40) normotensive subjects, constructed from the time shifted waveform PPW and the waveform PVW, denoted earlier as 6 and 7 respectively. The rise (pressurizing) portion of the pulse pressure versus pulse volume is shown as 19, and the fall (depressurizing) portion is denoted as 20. Note that the fall portion 20 of the plot experiences load/unload cycles as denoted by 21.

As depicted in FIG. 5, the three (3) component thick wall anelastic power law model denoted as 22, with inner wall radius 23 and outer wall radius 24, fitted to the normalized arterial pulse pressure versus normalized arterial pulse volume for the forty (40) normotensive subjects.

$$\left(\frac{\delta A}{A}\right) = \left(\frac{\beta_S \Delta P}{G_R\left(1-\left(\frac{a}{b}\right)^{2\beta_S}\right)}\right)\left[1-\left(\frac{\Delta P - P}{\Delta P}\right)^{\beta_S}\right] \quad (1)$$

The anelastic power law model is an analytical closed form solution of an incompressible material described by equation (1) for the systolic, pressurizing (loading) path, with a similar equation for the diastolic, depressurizing (unloading) path. The anelastic model has a power law coefficient for the systolic portion, $\beta_S$, and the diastolic portion, $\beta_D$, where ($\delta A/A$) is the change in area over original area at a pulse pressure of P. $\Delta P$ is systolic pressure minus diastolic pressure, $G_R$ is the radial secant shear modulus, $\beta_S$ is a power law coefficient for the systolic, i.e. loading (pressurizing) path, a is the inner wall radius, b is the outer wall radius, and $\beta_D$ is a power law coefficient for the diastolic, i.e. depressurizing (unloading) path. For a $\beta_S=1$, the model is linear elastic, for $\beta_S<1$, the model softens with increasing pressure, and for $\beta_S>1$, the model stiffens with increasing pressure. The simple anelastic power law model has been used to model arteries, both large and small, the aorta, the arterioles and veins. The small and large arteries have similar power law coefficients of $\beta_S<1$ at rest and $\beta_S>1$ when vasodilated, while the aorta is much different having $\beta_S>1$, as do the arterioles.

The normalized arterial pulse pressure (P) versus normalized arterial pulse volume, being the change in area over original area, i.e. (A/A) of the three component thick wall anelastic power law model fitted to the normotensive subjects data, is shown in FIG. 5. The rise (pressurizing) portion of the pulse pressure versus pulse volume for the power law model fitted to the measured data, is shown as 25, with a power law model value of $\beta_S=0.8$, and the purely fall (depressurizing) portion is denoted as 26, with a power law model value of $\beta_D=0.4$. As the arterial blood vessels are anelastic, they experience small load/unload cycles as the various pulse waves of the waveform arrive, as denoted by 21. The anelasticity of the model is given by the Quality factor, Q, which is the inverse of the energy lost divided by the total energy over a complete load/unload cycle. The Quality factor is related to the power law loading and unloading coefficients as given by equation (2).

$$Q^{-1} = \frac{1 - \beta_P \beta_D}{1 + 2\beta_D + \beta_P \beta_D} \quad (2)$$

The area between the load/unload paths 25 and 26 is the energy lost during a complete load/unload cycle. For a $\beta$ of 1 the model is linear elastic and thus Q tends to infinity, i.e. zero energy loss. The Quality factor, Q, for the fitted model shown in FIG. 5 is equal to 3.1, being considered the expected value of healthy arterial vascular blood vessels in vivo.

The blood vessels are composed of collagen (endothelium), elastin, smooth muscles and connective tissue. The arteries and veins differ significantly in their anelasticity, due to their significant different functions and applied loads. In the arteries, the collagen, elastin and smooth muscle have values of shear modulus in descending order of ~$10^7$ to $10^6$, and $10^5$ and $10^4$ $Nm^{-2}$, respectively. The arterial elastic lamellae and smooth muscle cells are wrapped by a network of collagenous fibrils. Most of the collagen fibers are orientated circumferentially, but some are orientated obliquely and others longitudinally. Elastin and collagen fibers contribute to the artery's elasticity. In humans, the number of elastic lamella is related to the anatomic location of the artery. Muscular arteries have only one internal and external elastic lamina, while in the aorta there are some 60-90 elastic lamina. The number of elastic lamina decreases gradually towards the periphery of the arterial system. Arterial wall viscoelasticity (anelastic) behavior plays a major role in regulating the mechanical behavior of muscular arteries to their applied loads. The smooth muscle component of the artery wall is considered an important element of the artery that contributes to its viscoelasticity, anelastic behavior. All components of the artery wall may contribute to its viscoelasticity, but the smooth muscle is the only component to respond to physiological stimulus. Furthermore, these components are influenced both by physiological and pathological changes in the mucopolysaccharide, in which they are embedded. The model could be made more complex with differing layers in the blood vessel wall, anisotropic properties, and also include time dependent effects. However, with that complexity the unique quantification to define the model parameters from non-invasive in vivo measurements becomes unwieldy, so a simple model that contains the essential behavior of the blood vessels' anelastic compliance is sort. Therefore, the three component model described here is considered a suitable choice. However, the method is not limited to this model's simplicity nor limited to a three component anelastic model, as a fourth component can be added to account for quantifying the effects of arterial vessels' axial tethering in vivo.

Figure 6:
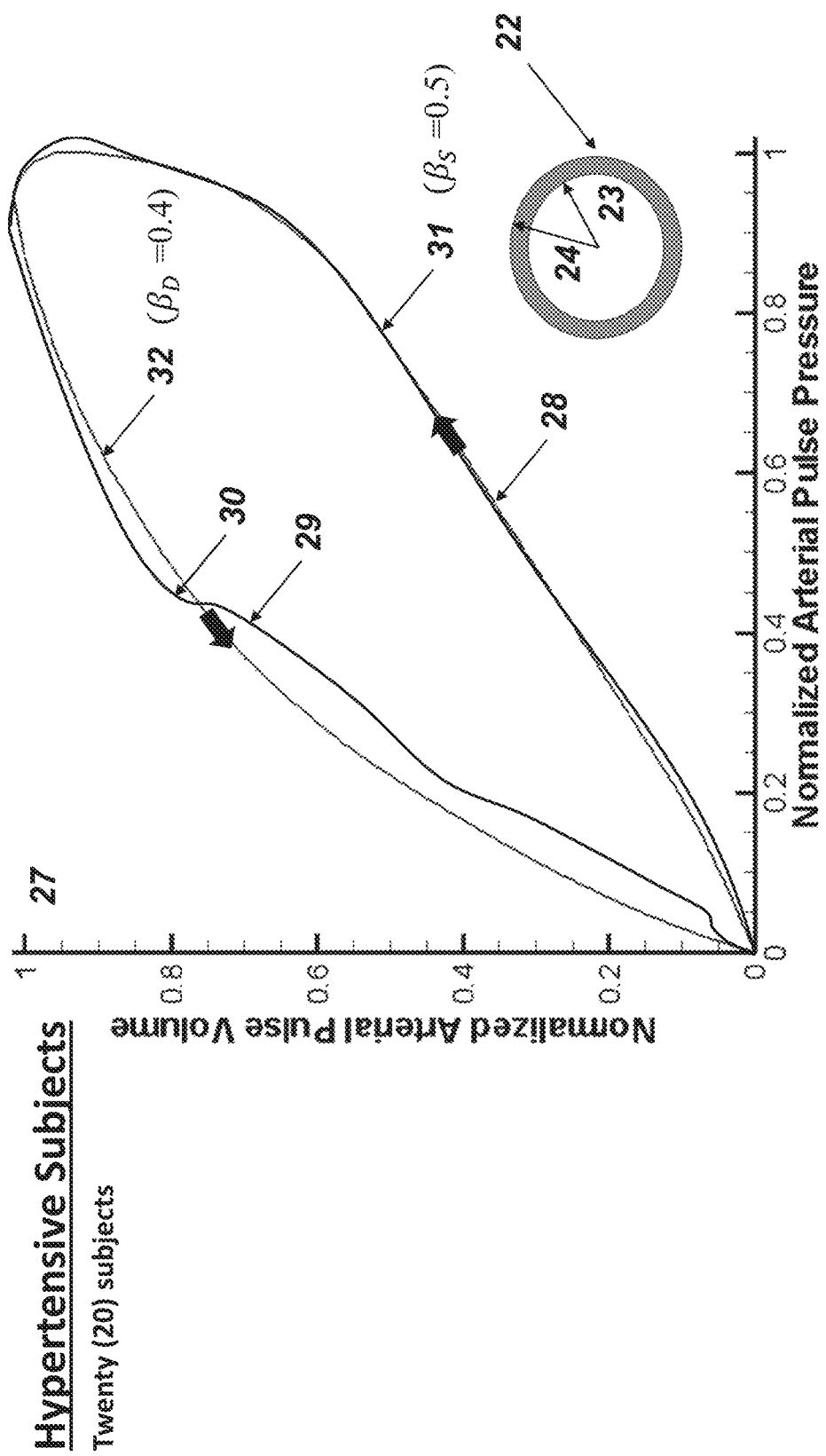
FIG. 6 is the normalized time shifted arterial pulse pressure plotted against the normalized arterial pulse volume as an average for twenty (20) hypertensive subjects, and the thick wall three (3) component anelastic power law model.

FIG. 6 depicts the normalized arterial pulse pressure (P) versus the normalized arterial pulse volume, being change in area over original area (A/A) for the twenty (20) hypertensive subjects, denoted as 27, constructed from the time shifted waveform PPW and the waveform PVW, denoted earlier as 6 and 7 respectively. The rise (pressurizing) portion of the pulse pressure versus pulse volume is shown as 28, and the fall (depressurizing) portion is denoted as 29. As the arterial blood vessels are anelastic, they experience small load/unload cycles as the various pulse waves of the waveform arrive, as denoted by 30. The three (3) component thick wall anelastic power law model denoted as 22, with inner wall radius 23 and outer wall radius 24, is fitted to the normalized arterial pulse pressure (P) versus normalized arterial pulse volume, being the change in area over original area, i.e. (A/A) for the twenty (20) hypertensive subjects. The rise (pressurizing) portion of the pulse pressure versus pulse volume for the power law model fitted to the measured data, is shown as 31, with a power law model value of $\beta_P=0.5$, and the purely fall (depressurizing) portion is denoted as 32, with a power law model value of $\beta_D=0.4$. The Quality factor, Q, for the fitted model shown as 27 in FIG. 6 is Q=2.5, which translates to a 40% energy loss over a complete load/unload cycle, is considered representative of unhealthy arterial vascular blood vessels.

Figure 7:
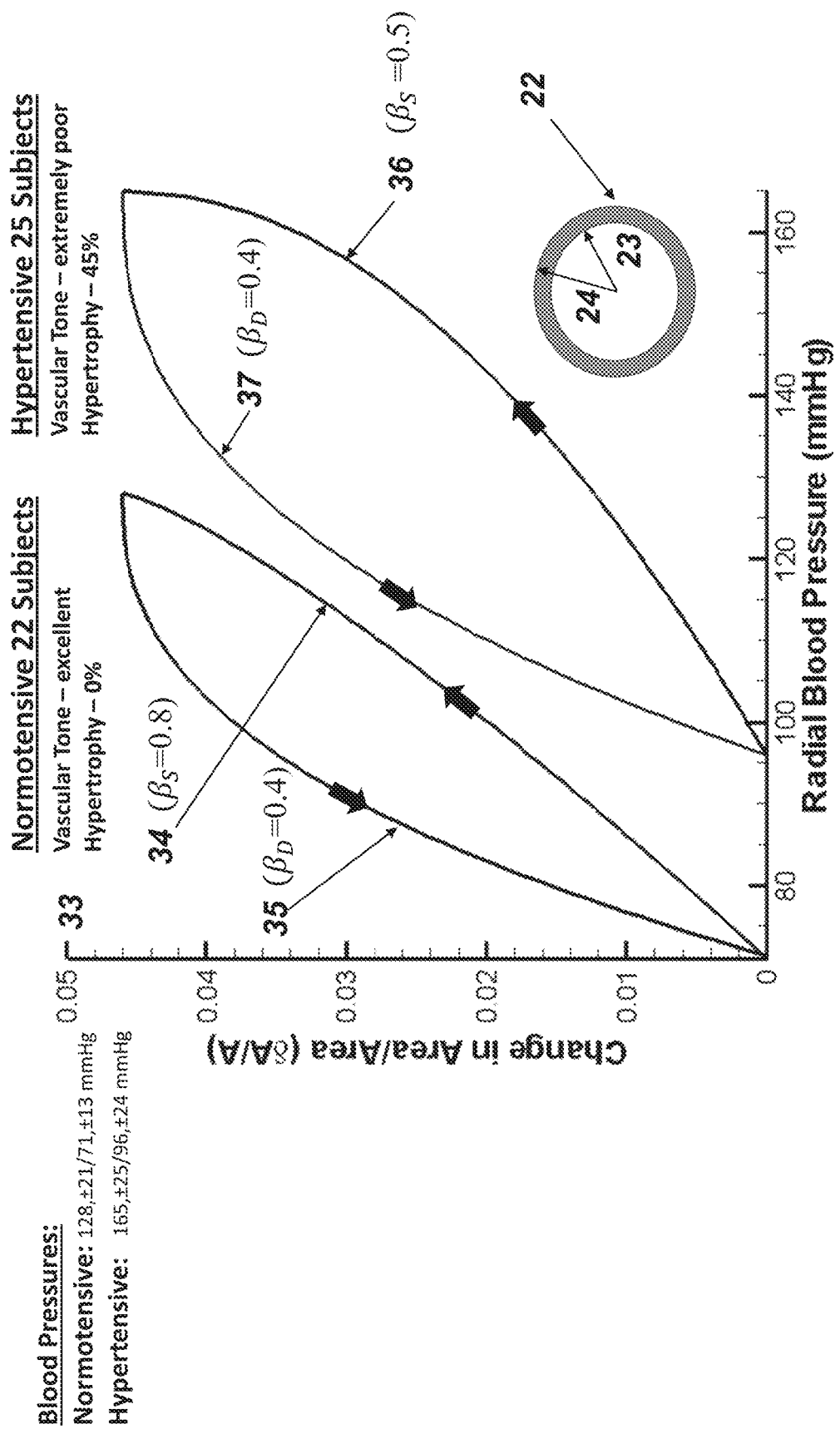
FIG. 7 is the time shifted arterial pulse pressure plotted against the arterial pulse volume as an average for twenty two (22) normotensive and twenty five (25) hypertensive subjects experiencing significant hypertrophy, and the thick wall three (3) component anelastic power law model.

FIG. 7 depicts the averaged pulse radial arterial change in area over original area versus radial artery pulse pressure for twenty two (22) normotensive subjects (ranging from 25 to 64 years, mean±SD, 44±11 years) and twenty five (25) hypertensive subjects (ranging from 28 to 72 years, mean±SD, 48±12 years), as detailed in Laurent et al. (1994). The normotensive subjects had blood pressures of 128±21/71±13 mmHg, and the hypertensive subjects had blood pressures of 165±25/96±24 mmHg. The anelastic model fitted data are shown in FIG. 7 as 33, with the pressurizing path of the normotensive subjects being denoted as 34, and the depressurizing path as 35. The pressurizing path for the hypertensive subjects is denoted as 36 and the depressurizing path as 37. The hypertensive subjects all had significant hypertrophy of the radial artery. Comparing the two groups at their respective mean arterial pressures, both groups had similar internal diameters, (internal diastolic diameter 2.53±0.32 and 2.50±0.56 mm), but significantly different intima-media thickness (0.40±0.06 mm and 0.28±0.05 mm, P<0.001) for the hypertensive and normotensive subjects, respectively. Thus, the hypertrophy of the hypertensive group was 43%, being the percentage of growth of the intima-media thickness of the hypertensive group compared to the normotensive group. The anelastic model computed secant shear modulus ($G_R$) values of 510 kPa and 410 kPa for the normotensive and hypertensive subjects respectively, and even though the shear modulus was less in the hypertensive group, the significant hypertrophy thus yielded the same circumferential strain at the inner artery wall at their respective systolic pressures for both groups; highlighting that hypertrophy growth is a means of combating loss of tone, i.e. decreasing values of $\beta_S$ of the hypertensive subjects compared to the normotensive subjects.

Figure 8:
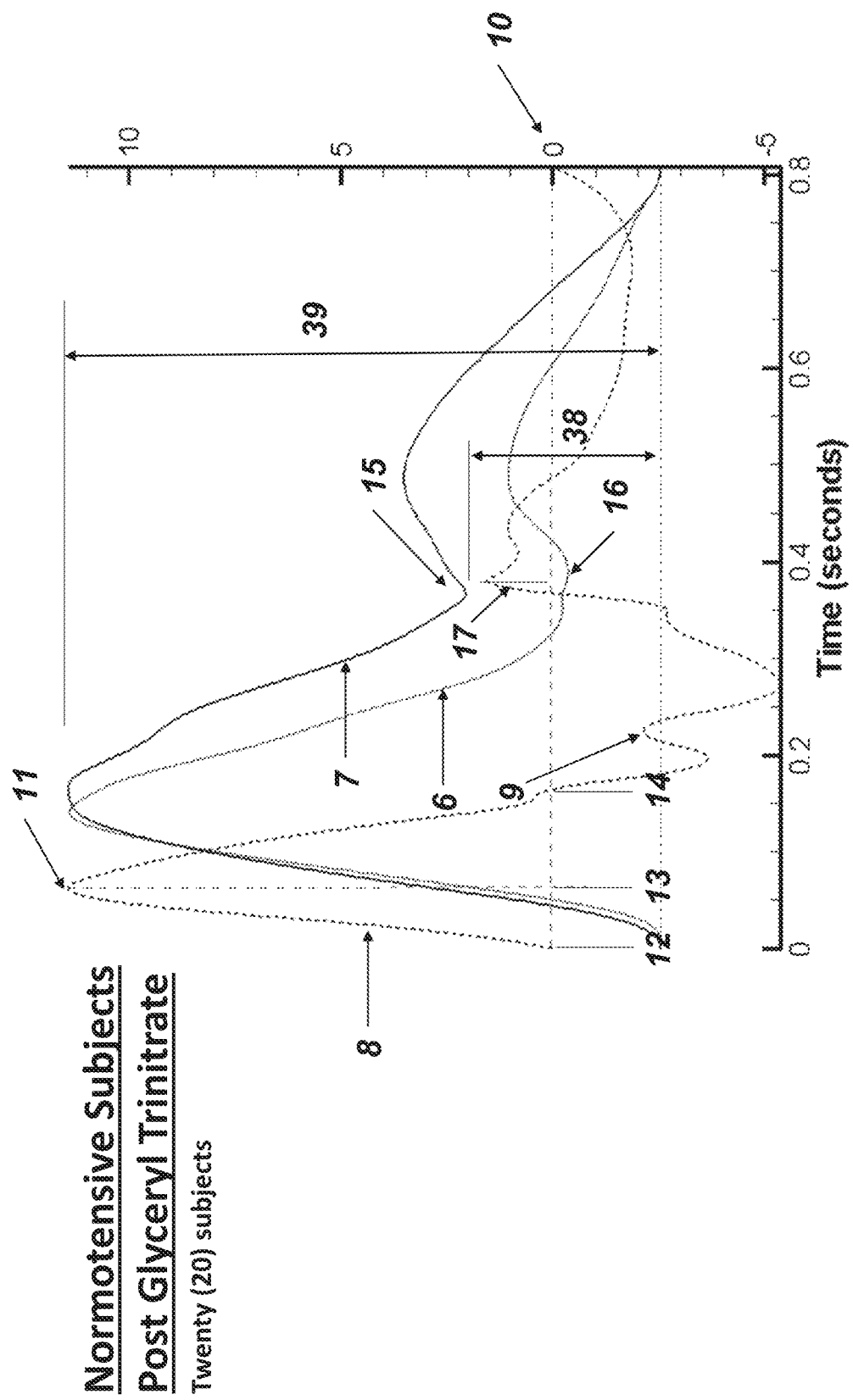
FIG. 8 is the averaged normalized time history, for a subset of twenty (20) of the forty (40) normotensive subjects following sublingually administration of 500 μg of glyceryl trinitrate (NTG), of the peripheral pulse optical plethysmograph waveform (PVW) recorded from an optical plethysmograph sensor positioned over a finger, and the time history of the constructed first time derivative of the PVW, and the averaged time history of the peripheral arterial pulse pressure waveform (PPW) recorded over the radial artery.

FIG. 8 depicts the averaged normalized one heart cycle time history for a subset of twenty (20) of the forty (40) normotensive subjects following sublingual administration of 500 μg of glyceryl trinitrate (NTG). FIG. 8 shows the peripheral pulse optical plethysmograph waveform (PVW), denoted as 7, recorded from an optical plethysmograph sensor positioned over a finger, the time history of the constructed first time derivative of the waveform PVW being the dPVW, denoted as 8, and the averaged normalized time history of the peripheral arterial pulse pressure waveform (PPW) recorded over the radial artery by applanation tonometry by a piezo-resistive cantilever transducer, denoted as 6. The waveforms were recorded 3 minutes after the NTG was administered, which is when the effects of the NTG are at a maximum. The zero ordinate of the dPVW constructed waveform is shown as 10. The first pulse wave peak is denoted as 11. The rise and fall time intervals of the first pulse wave are given by the difference in the time abscissa of points denoted as 12, 13 and 14. With the points, being the intersection of the zero ordinate 10 and the constructed waveform dPVW, point 12 being the start of the rise of the first pulse wave, point 13 being the maximum of the first pulse wave, and point 14 being the end of the fall of the first pulse wave. The ratio of the fall time to the rise time of the first pulse wave for the normotensive subjects as determined from points 12, 13 and 14 is 1.8, which is the same as the forty (40) normotensive subjects prior to any NTG being administered. That is, the NTG had no discernable effect on this fall to rise time ratio of the first pulse wave. The second forward pulse wave is shown as 15 on the pulse volume waveform PVW, 7, and is also shown as 16 on the measured pulse pressure waveform, 6. The second forward pulse wave, which causes closure of the aortic valve, is shown as 17 on the dPVW waveform. The second forward pulse wave peak arrival time location is 0.38 seconds, which is virtually the same as the forty (40) normotensive subjects prior to any NTG being administered.

Note the significant differences in the second forward pulse wave in FIG. 8, i.e. with NTG having taken effect, compared to that shown in FIG. 3 for the subjects prior to any NTG being administered. The second forward pulse wave in FIG. 3 is 0.65 of the maximum pulse volume, and in FIG. 8 it is 0.31, denoted as the ratio of 38 to 39, and in this case being a percentage drop of 48% from the forty (40) normotensive subjects to the twenty (20) subset normotensive subjects following NTG administration. Similarly, the pulse pressure drops significantly, from 0.31 in FIG. 3, prior to NTG being administered, to 0.16, after NTG, as shown in FIG. 8, for the normotensive subjects prior and after NTG being administered. The ratio of the normalized pulse volume decline or rise, is a quantitative indicator of the extent of vasodilation or vasocontraction, as also are the changes in $\beta_S$.

Figure 9:
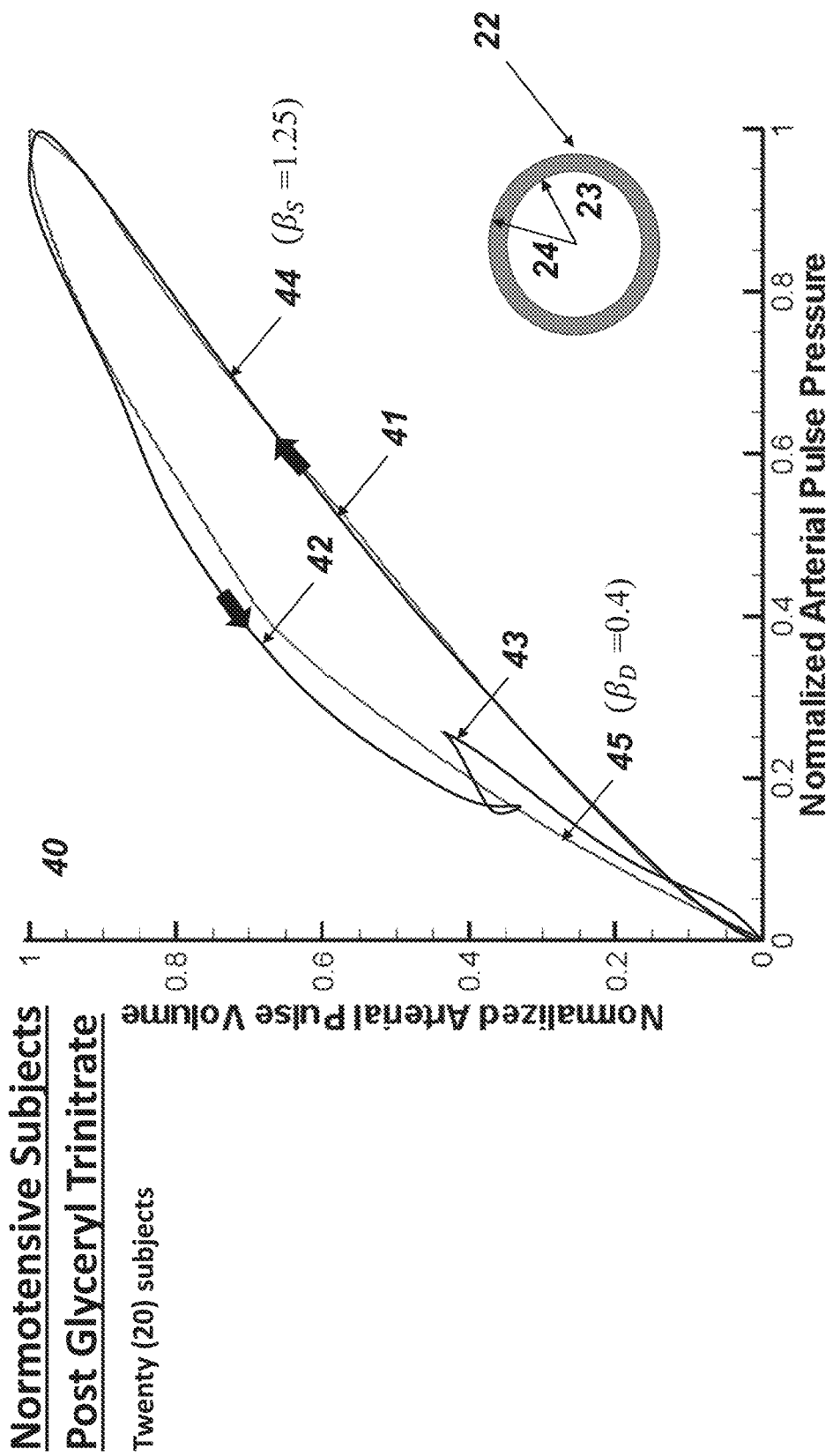
FIG. 9 is the normalized time shifted arterial pulse pressure plotted against the normalized arterial pulse volume as an average for the subset of twenty (20) normotensive subjects, following three (3) minutes after sublingually administration of 500 μg of glyceryl trinitrate (NTG), and the thick wall three (3) component anelastic power law model.

FIG. 9 depicts the normalized arterial pulse pressure versus normalized arterial pulse volume for the subset of twenty (20) of the forty (40) normotensive subjects, three (3) minutes after NTG administered, denoted as 40, constructed from the waveforms PPW and PVW, denoted earlier as 6 and 7 respectively. The rise (pressurizing) portion of the pulse pressure versus pulse volume is shown as 41, and the fall (depressurizing) portion is denoted as 42. As the arterial blood vessels are anelastic, they experience small load/unload cycles as the various pulse waves of the waveform arrive, as denoted by 43. The three (3) component thick wall anelastic power law model denoted as 22, with inner wall radius 23 and outer wall radius 24, is fitted to the normalized arterial pulse pressure ($\Delta P$) versus normalized arterial pulse volume ($\Delta V/V$) for the twenty (20) subset of the forty (40) normotensive subjects, subjected to the effects of vasodilation due to NTG being administered. The rise (pressurizing) portion of the pulse pressure versus pulse volume for the power law model fitted to the measured data, is shown as 44, with a power law model value of $\beta_S=1.25$, and the purely fall (depressurizing) portion is denoted as 45, with a power law model value of $\beta_D=0.4$. The Quality factor, Q, for the fitted model shown as 40 in FIG. 9 is Q=4.6, which translates to a 22% energy loss over a complete load/unload cycle, significantly different to the forty (40) normotensive subjects having a Q=3.1. The Quality Factor of Q=4.6 is considered representative of healthy arterial vascular blood vessels, subject to significant vasodilation.

Note the significant difference in the rise (pressurizing) portion of 41 compared to 19, shown in FIG. 5, for the normotensive subjects prior to NTG being administered. The $\beta_S$ value of >1 in FIG. 9, leads to a blood vessel stiffening with pulse pressure, clearly resulting in a significant change in the anelastic response of the arterial vessels to pulse pressure, both loading and unloading, due to vasodilation. In this case of vasodilation, the pulse volume response leads the pulse pressure response up to near the peak pulse volume; whereas, in the normotensive and hypertensive subjects, the pulse pressure leads the pulse volume response with time, during the rise (pressurizing) portion of the arterial vessels. It is the significant changes in the arterial blood vessels anelastic behavior under vasodilation, that result in the observed large drops in normalized pulse volume and normalized pulse pressure during diastolic. The reflected waves are not removed by the vasodilation, but the forward waves including the first pulse wave require a significantly larger pulse volume to achieve the same pulse pressure, i.e. when pressurizing up the path 41, compared to pressurizing up the path 19, as is the case for the normotensive subjects. Thus, any forward waves result in much lower induced pulse pressure for the dilated arteries, and their reflected components are also reduced. In the depressurizing state, a small change in pulse volume results in a significant change in pulse pressure, i.e. following path 42 compared to 20, and thus accounts for the large changes seen in the diastolic phase.

Induced vasocontraction is analogous to a negative pressure applied to the inner wall of the arterial blood vessels, and thus unloads the vessels along the unloading path of the anelastic model. Thus, for a very small contraction pressure, a moderate contraction volume change is achieved, requiring a rise in internal pressure to overcome the vasocontraction. Further increase in pulse pressure follows the loading (pressurizing) path, similar to the hypertensive subjects as denoted by the anelastic model as 31, and then on unloading (depressurizing) the path denoted as 32, as shown in FIG. 5. Significant vasocontraction results in a high Q value, thus giving rise to significant damping of the high frequency shear waves. The contracted arteries unload (depressurize) along the path denoted as 32, but the arterial pressure remaining, as mentioned earlier to overcome the vasocontraction effect, will only dissipate by arterial Windkessel flow, and can be ~20% of the maximum pulse pressure. This impact results in the fall to rise time ratio of the first pulse wave to be <1 for the case of vasocontraction, as the early rise in pulse pressure has no induced pulse volume change, and so the initial rise time of the first pulse wave will be longer than the fall time. Therefore, vasocontraction not only increases the diastolic arterial pressure quite significantly for a small applied contraction pressure, but also increases the pulse pressure, and combined, significantly raises the systolic arterial pressure.

Figure 10:
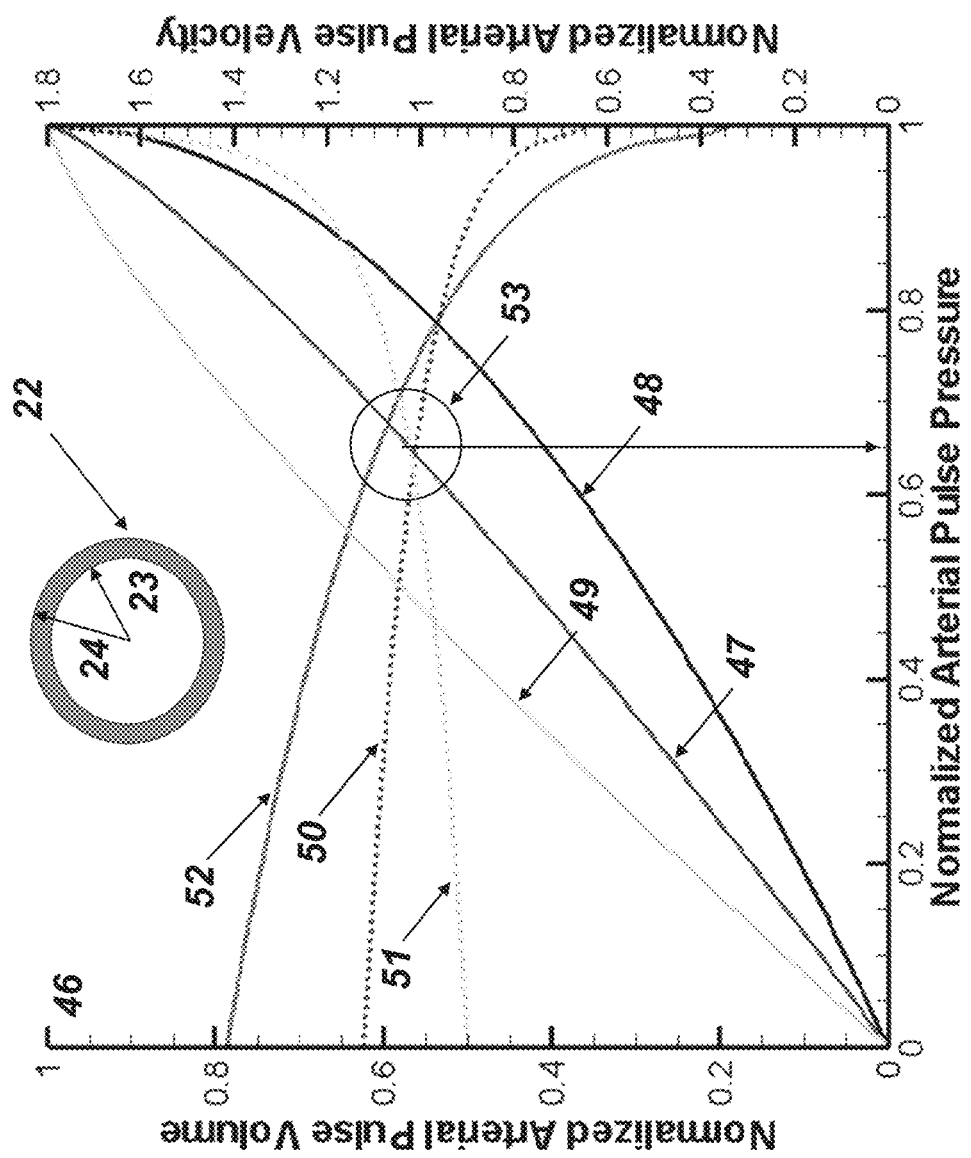
FIG. 10 is the normalized time shifted arterial pulse pressure plotted against the normalized arterial pulse volume and the normalized arterial pulse wave velocity for the pressurizing phase of the arteries, as an average of the forty (40) normotensive subjects, of the twenty (20) hypertensive subjects, and of the subset of twenty (20) normotensive subjects, following three (3) minutes after sublingually administration of 500 μg of glyceryl trinitrate (NTG), and the thick wall three (3) component anelastic power law model.

FIG. 10 depicts the normalized arterial pulse volume plotted against the normalized arterial pulse pressure 46, for the normotensive group, hypertensive group, and the normotensive subset group subjected to NTG for the pressurizing phase only, being denoted as 47, 48 and 49 respectively. Their respective normalized arterial pulse velocities are shown as denoted by 50, 51 and 52 respectively. Note the significant change in pulse velocity for all three groups as a function of pulse pressure. At 65% of the normalized pulse pressure, all three groups have normalized arterial pulse velocities all virtually the same, at a normalized value of 1.0, as denoted by 53.

Figure 11:
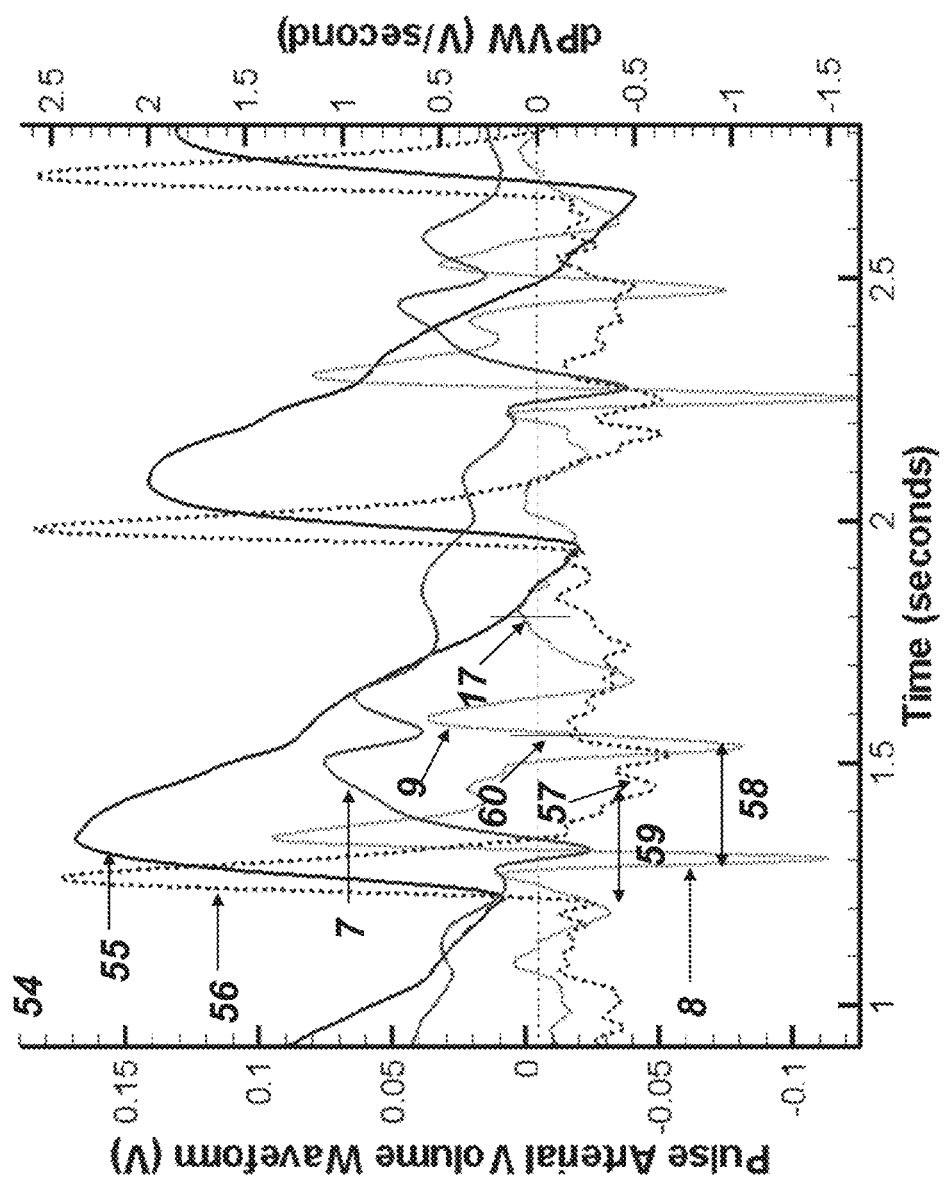
FIG. 11 is the time history of the peripheral pulse volume waveform (PVW), before and after exercise, recorded from an optical plethysmograph sensor positioned over the radial artery, and the time history of the constructed first time derivative of the PVWs.

FIG. 11 depicts the time histories 54 of the waveform PVW 7, measured over the radial artery by the disclosed processing device. The first time derivative dPVW is shown as 8. These waveforms were collected on a mildly hypertensive male of 69 years of age before exercise. After exercise the same waveforms were collected and constructed as denoted by 55 and 56. Note the significant increase in amplitude in the waveform PVW after exercise, comparing 55 to 7, and the reduction in the amplitude of the prime reflective wave, 9 versus 57. Interestingly, the prime reflective wave arrival time, being a two way travel time, are virtually the same, 58 and 59, being 0.23 seconds before exercise and 0.24 seconds after exercise. The pulse wave velocity measured from the subject's brachial artery at the elbow to the radial artery, yielded a pulse wave velocity of 6.9 m/sec. The prime reflected wave is assessed to be reflected from the fingertips, back to the upper arm pit, where due to the numerous arteries (axillary, subclavian, etc.) the wave is reflected back down the brachial artery to the radial artery, for a two wave travel path for this subject of 1.6 m for a pulse wave velocity of 6.6 m/sec prior to exercise, and 6.3 m/sec after exercise. The pulse pressure experienced by the prime reflected wave, integrated over its travel path using the waveform PPW is 65% of the arterial maximum pulse pressure, and thus explains why there is little to no difference in the arrival time of the prime reflected wave in the before exercise and after exercise conditions, even though there are significant differences in pulse pressure, and the significant dependence of pulse wave velocity on arterial pulse pressure as shown in FIG. 10.

From waveforms PPW and PVW of the mildly hypertensive 69 year old male subject of FIG. 11, the systolic power law coefficient was determined as 0.67, being midway between the normotensive and hypertensive subjects given in FIG. 5 and FIG. 6. Assuming a linear relationship between hypertrophy and the systolic power law coefficient, the a/b ratio of the mildly hypertensive 69 year old male subject is 0.785, from data given in FIG. 7, for a/b=0.81 and 0.75 for the normotensive and hypertensive subjects, respectively.

The tube wave or Stoneley wave as it is generally referred to in geophysics, is a fluid wave travelling in a borehole, and has been extensively studied, originating from the pioneering work of Biot in the 1950s. The conical wake of excited shear waves generated by the Stoneley wave in a slow medium was first observed in the early 1960s. In arterial biomechanics, it appears that the wake of pulse generated high frequency highly dispersive shear waves has been overlooked, even though they are clearly evident in the peripheral arteries, both small and large, in the aorta, and the veins. In optical coherence tomography, the physics is well known and utilized. By focusing the ultrasonic "pushing" beam at a speed greater than the tissue shear wave speed, a wake of excited intense shear waves are generated along a Mach cone creating a plane of intense shear waves propagating in opposite directions. The arterial and venous pulses excite a wake of high frequency shear waves with a Mach angle of 90°, so the shear waves propagate along the vascular vessels as a guided wave. The pulse generated wake of high frequency shear waves gives rise to oscillatory pressure and suction waves acting on the vascular vessel, which have been consistently misinterpreted in the literature in the carotid, brachial and radial as reflected pressure and suction waves. The wake of pulse generated high frequency shear waves also occur in the veins, but at much lower amplitudes than the arteries.

The wake of intense excited shear waves, generated by the traveling pulse, have a particle motion perpendicular to the axial (longitudinal) arterial direction, thus setting up periodic oscillatory waves of pressure and suction, that are highly dispersive. Note that the excited shear wave intensity is much less after exercise compared to at rest. During exercise the vascular smooth muscle relaxes and the radial secant shear modulus ($G_R$) drops significantly, resulting in the radial Bramwell-Hill wave speed being much lower during exercise compared to at rest. The amplitude of the excited shear waves is dependent on the ratio ($C_{BH}/C_L$), i.e. the radial Bramwell-Hill wave speed to the longitudinal shear wave speed, the greater the ratio the higher the induced shear wave amplitude. Since the contrast between the radial and longitudinal wave speeds during exercise compared to at rest is less, then the pulse excited wake of shear waves has a lower amplitude during exercise compared to at rest.

The formulation of the PWV in the arteries, follows the same procedure as outlined in the geophysics literature, with the p-wave wave speed of the fluid in the geophysics case being substituted by the radial Bramwell-Hill wave speed. The artery longitudinal shear modulus, incorporating the arterial longitudinal wave shear modulus plus arterial embedment and tethering. Assuming the same density for blood and tissue, then the arterial PWV is given by equation (3) as detailed below:

$$c_P = \frac{c_{BH} c_L}{\sqrt{c_{BH}^2 + c_L^2}} \quad (3)$$

where $C_P$ is the arterial pulse wave speed, being the PWV. $C_{BH}$ is the arterial radial Bramwell-Hill wave speed, being the Frank/Bramwell-Hill Equation, given by $$c_{BH}^2 = \frac{A \delta P}{\rho \delta A},$$

where $\rho C^2_{BH} = G_{BH}$ with $G_{BH}$ being the Bramwell-Hill modulus. $C_L$ is the arterial longitudinal shear wave speed, which includes the effects of artery embedment and tethering, with $\rho C^2_L = G_L$ the arterial longitudinal shear modulus. The PWV is significantly different from the $C_{BH}$, especially in the peripheral arteries, due to the artery longitudinal shear wave speed $C_L$ being much lower than radial $C_{BH}$ wave speed.

Knowing the subject's two PWVs ($C_P$), at rest and after exercise, then $C_L$ and the two secant $C_{BH}$ wave speeds (at rest and after exercise) can be determined from equation (3). By measuring a subject's left radial waveforms PPW and PVW, both at rest and after exercise, the secant anelastic properties of the artery can be determined. The prime reflective pressure wave in the left arm is reflected from the fingertips and back from under the armpit. From the subject's left arm length, and the two wave travel times for at rest and after exercise, $C_P$ at rest and after exercise can be found. This reflective wave travels along the arm from systole to below mid-diastole. The $C_{BH}$ wave speed of the prime reflected pressure wave is the tangential $C_{BH}$ velocity at mid-diastole. The diastolic portion is subject insensitive and the tangential $C_{BH}$ at mid-diastole is almost exactly the same as the systolic secant $C_{BH}$ for all subjects.

From the ratio of the waveforms PPWs and the PVWs at systole, two equations derived from (3) for at rest and after exercise, can be solved for the respective $\delta A/A$s at systole and the secant $C_L$ at systole, provided one of the APs, either at rest or after exercise is known. Due to the significant change in pulse pressure following exercise any delay in measuring $\Delta P$ will result in significant error, thus the at rest $\Delta P$ is preferred to be used. As given in FIG. 11 a mildly hypertensive 69 yr old male had $C_P$ of 6.6 m/s and 6.3 m/s at rest and after exercise, and PPW and PVW ratios of at rest to after exercise of 0.61 and 0.49. Solving the two equations, yields radial secant Bramwell-Hill wave speeds ($C_{BH}$) of 10.5 m/s and 9.4 m/s for at rest and after exercise, and a $C_L$ of 8.5 m/s. The subject's at rest $\Delta P$ was 42 mmHg, yielding a $\delta A/A$ at systole of 0.049 for the at rest state, and a $\delta A/A$ at systole of 0.1 for after exercise.

Assuming a density of blood and tissue of 1040 Kgm/m³, the subject's left arm longitudinal secant shear modulus $G_L$ is 75 kPa, compared to the radial secant Bramwell-Hill ($G_{BH}$) moduli of 115 kPa and 95 kPa, for before and after exercise. That is, the pulse wave is travelling in a "slow" medium, and the pulse generates and excites a wake of high frequency highly dissipative shear waves, that produce oscillatory pressure and suction waves on the vascular vessel, be it an artery or vein. These shear wave induced oscillatory pressure and suction waves have been misidentified in the past as reflective pressure waves, since wave intensity analysis can't discern and differentiate between the pulse exited wake of shear waves from other traveling waves. Relaxation of the vascular smooth muscle during exercise significantly reduced the radial secant modulus $G_{BH}$ by 18%, i.e. from 115 kPa to 95 kPa. For younger healthy subjects, the reduction in the radial secant modulus $G_{BH}$ by smooth muscle relaxation during exercise can be much greater.

The above coupling of the PWV with the arterial longitudinal shear modulus ($G_L$), which includes the effects of artery embedment and tethering, highlights why PWV is a poor indicator of the biomechanical properties of arteries, both small and large. Reanalysis of earlier experimental work has shown that significant systemic changes occur in HT subjects, which have earlier been overlooked and have led to conclusions, that the stiffnesses of peripheral arteries increase less or not at all with increasing age or hypertension. As shown here, from a reanalysis of historical data, the peripheral radial artery shows significant changes in its biomechanical properties due to hypertension. The systolic power law coefficient changes from 0.8 (NT) to 0.5 (HT), the radial secant shear modulus drops from NT to HT, hypertrophy is added in HT subjects, and the overall stiffness of the artery is increased in HT subjects.

Figures 12A, 12B, 12C:
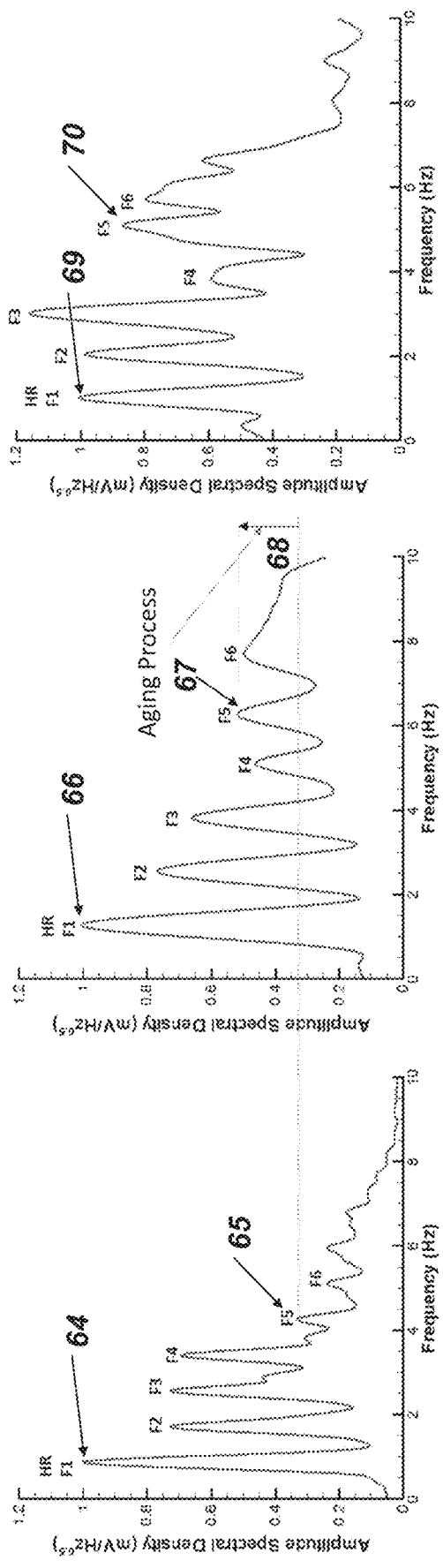
FIG. 12A is the power spectral density of the first time derivative of PVW over the radial artery for a 32 year old normotensive male, with the ratio of the fifth to the first harmonic shown.
FIG. 12B is the power spectral density of the first time derivative of PVW over the radial artery for a 70 year old mildly hypertensive male, with the ratio of the fifth to the first harmonic shown.
FIG. 12C is the power spectral density of the first time derivative of PVW over the radial artery for a 34 year old hypertensive male, with the ratio of the fifth to the first harmonic shown.

FIGS. 12A, 12B and 12C depict the power spectral density versus frequency of the first time derivative of the PVW, as measured non-invasively over the radial artery. FIG. 12A is for a 32 year old normotensive male (Subject A), note the amplitude ratio of the fifth harmonic to the first harmonic (F5/F1), being the ratio of the ordinate of the point 65 to 64. The first harmonic is the heart beat rate. The ratio of F5/F1 is much lower compared to the F5/F1 ratio given in FIG. 12 B (Subject B) for a 70 year old mildly hypertensive male, i.e. the ratio of the ordinate values of point 67 over point 66. The increase in the F5/F1 ratio from FIG. 12A to FIG. 12B is due to the nature ageing process. Shown in FIG. 12C is the F5/F1 ratio (the ordinate value of point 69, over that of point 68) for a 34 year old hypertensive male, denoted as Subject C. Note the significant difference in the ratios from FIG. 12A to FIG. 12C. The significance of the fifth harmonic is not only of significant interest in hypertension, and pulse wave speed, but also in blood flow as denoted by the Womersley's number for pulsating flow in larger arteries, as the flow velocity is out of phase with the driving pressure gradient, due to the flow gradient being time variant. The Womersley's number $\alpha$ is given by $R(\rho\omega/\eta)^{1/2}$, where R is the radius, p blood density, n apparent blood viscosity, and w is the angular frequency, typically taken for that of the fifth harmonic. The oscillatory nature of the pulsating flow is critical not only for flow driving dynamics, but also the pulsating induced shear stresses applied to the arterial walls, as experienced by the endothelium. The amplitude ratio of F5/F1 could also be constructed from the first time derivatives of the PPW and PUW waveforms, rather than the PVW shown in FIG. 12.

Figure 13:
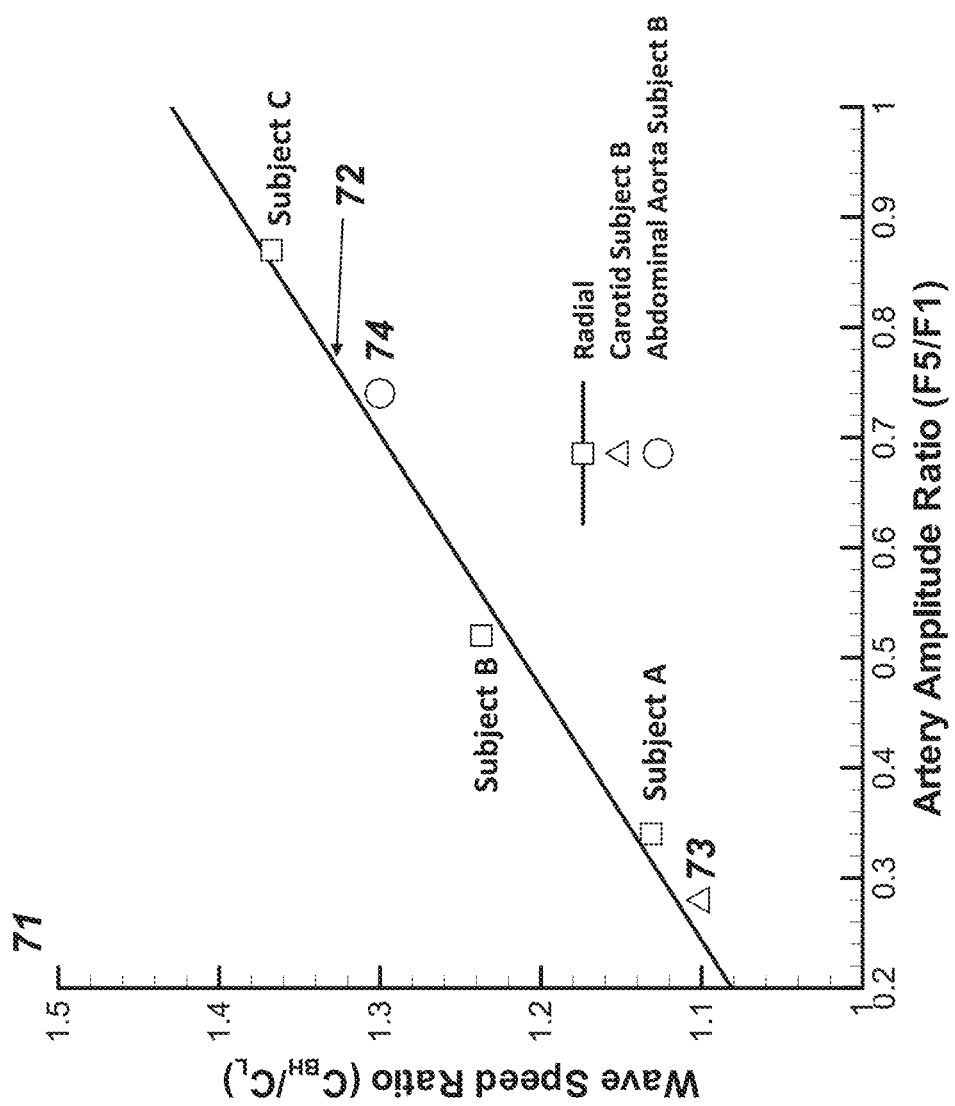
FIG. 13 is the amplitude ratio of the fifth to the first harmonic from the power spectral density of the first time derivate of PVW versus the wave speed ratio of the $C_{BH}$ (Bramwell-Hill radial wave speed) to the $C_L$ (longitudinal wave speed) for the subjects in FIG. 10 A, B & C for their radial and carotid arteries.

FIG. 13 depicts the arterial F5/F1 ratio for the three earlier subjects plotted against the ratio of their wave speed ratio $C_{BH}/C_L$ (point 70) as measured over the subjects' radial artery. The correlation of these ratios is virtually linear as shown by 71. Also shown in FIG. 13 is the respective ratios over Subject B for the carotid and abdominal aorta, as shown by points 72 and 73. Point 72 was constructed from power spectral density of the first time derivative of the PVW; whilst point 73 was constructed from the first time derivative of the PUW, due to the depth of the abdominal aorta for non-invasive measurement. A more extensive dataset for the ratios of F5/F1 to $C_{BH}/C_L$ would enable a simple means of determining the $C_L$ and $C_{BH}$ wave speeds from the PWV for a subject's arteries.

FIGS. 14A and 14B show the PPW, as denoted by 6, and the PVW, given by 7, over the radial artery of Subject B as measured by the device 3, for 74 at a low strap tension, and 75 for a higher strap pressure. The device 3 measures by a force sensor the normal pressure applied to the artery from the device's strap tension. The strap tension that enables the device to measure PPW as a tonometer, flattens the artery and thus produces an artifact in the PVW during late diastolic to mid-systole, as given in FIG. 14A by point 76. The point 76 for the PVW coincides with the normal pressure applied by the strap as shown by height 77 of the PPW waveform. The applied normal pressure applied by the strap is equivalent to the PPW ordinate ratio denoted by points 77 to 78, and thus is related to the pulse pressure, i.e. the systolic minus diastolic blood pressures. The negative ordinate of the PVW is shown as 79 and the positive ordinate as 80. In FIG. 14B, denoted as 75, the same waveforms are shown, and similarly the point 81 coincides with the applied normal pressure from the higher strap tension, yielding the PPW ordinate ratio of 82 to 83, for the higher strap normal pressure to the blood pulse pressure. Also are measured the ordinate values of the PVW waveform given by points 84 and 85. Similarly the pulse blood pressure can be determined from this higher strap pressure, and provide a similar value as determined in 74 for a lower strap pressure. From the anelastic power law model, the ratio of the PPW ordinate values 83 over 78 to the power of RD is equal to negative ordinate values of PVW, being the ratio of points 84 to 79. Thus RD is determined directly from the two strap pressures without the need to construct a PPW versus PVW plot from a single strap pressure. Similarly, from the anelastic power law model, the ratio of the PPW ordinate values 83 over 78 to the power of $\beta_S$ is equal to the overall ordinate ratio of PVW, being the ratio of points, 85 plus the absolute value of 84, to 80 plus the absolute value of 79. Thus $\beta_S$ is determined directly from the two strap pressures without the need to construct a PPW versus PVW plot from a single strap pressure. Setting the normal pressure imposed on the artery for the high strap tension in 75 as $S_H$, and at the lower strap tension in 74 as $S_L$, then the diastolic pressure $\beta_D$ can be determined as the ratio of $(\beta_D-S_H)/(\beta_D-S_L)$ to the power of 1/RD is equal to the ratio of the negative ordinate values of PVW being points 79 over 84. From the above, the complete blood pressures at systole and diastole are determined. A subject's arterial tone, denoted by the anelastic power law coefficients, $\beta_S$ and $\beta_D$, at various states of vasodilation and vasocontraction do not change significantly over time, even with a strenuous training program. Therefore, provided data are collected periodically from two different strap normal pressures, the complete blood pressure, both systolic and diastolic, can be determined by a single strap normal pressure for a moderate time period.

Figure 15B:
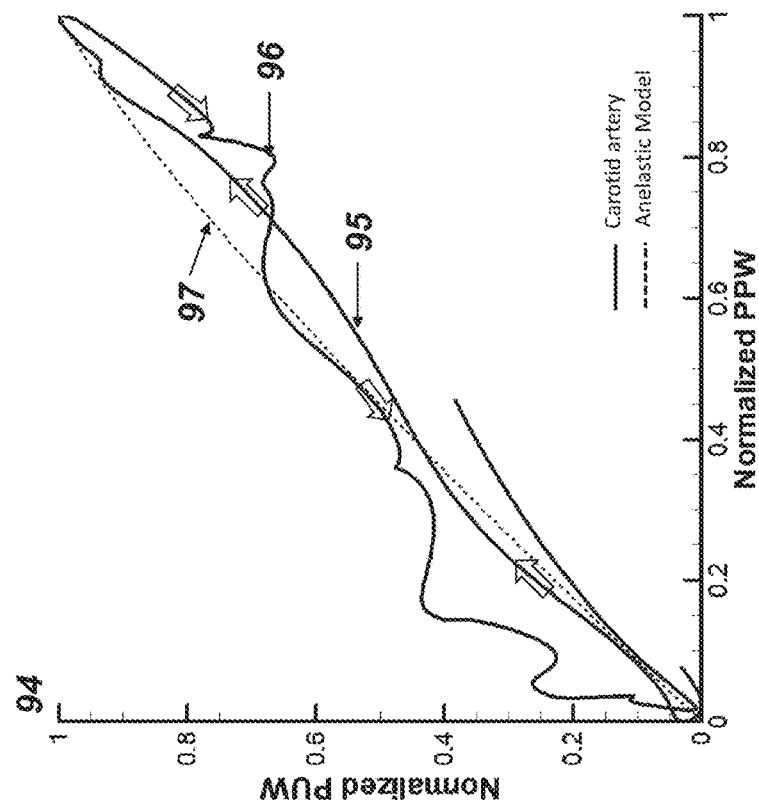
FIG. 15B is the time history of the peripheral pulse pressure waveform (PPW) versus pulse velocity waveform (PUW), recorded from the force and velocity sensors positioned over the carotid artery, and the calculated anelastic model of the systolic pulse velocity waveform.
Figure 15A:
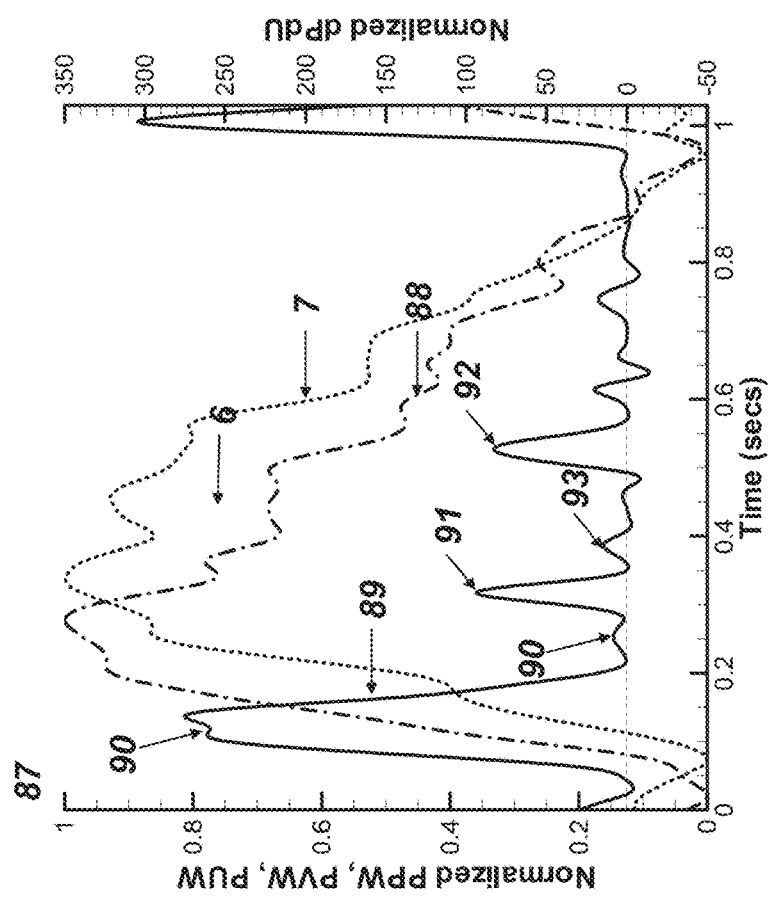
FIG. 15A is the time history of the peripheral pulse pressure waveform (PPW), pulse volume waveform (PVW) and velocity waveform (PUW), recorded from an optical plethysmograph, the force and velocity sensors positioned over the carotid artery, and the calculated wave intensity analysis (dPdU) waveform constructed from the waveforms PPW and PUW.

FIG. 15A depicts the normalized time histories 86 of waveforms PPW 6, PVW 7, and PUW 87 over a single cardiac cycle measured over the carotid artery by the disclosed processing device. These waveforms were collected on a mildly hypertensive male of 69 years of age at rest, i.e. before exercise, the same subject as given in FIG. 11 for the radial artery. Note that the waveforms PPW and PUW are virtually in-phase during the systolic phase, and only deviate during the diastolic phase. The waveforms PPW and PUW are related to $C_{BH}$ through the momentum jump (shock) condition for the special case when the flow velocity is negligible compared to the wave speed, i.e. $\delta P = \rho C_{BH} \delta U$. The anelastic power law model, equation (1) differentiated with respect to the pulse pressure, yields the tangential systolic velocity $C_{BH}$, and integrated over the characteristic quantifies the blood velocity as a function of pulse pressure. The wave intensity analysis waveform dPdU calculated from the waveforms PPW and PUW is shown as 88. Positive values of dPdU are forward traveling waves and negative values are backward traveling waves. The zero ordinate of dPdU is shown as a dotted line. Note, there are virtually no backward waves observed in the carotid artery, which is in stark contrast to the radial artery where numerous reflected waves are observed.

The pulse excited wake of high frequency shear waves result in oscillatory pressure and suction waves, as shown by 89 and 90. The period of these shear waves is given by the time abscissa values of the points 89 and 90 and for this subject has a period of ~0.18 secs compared to his left radial artery of 0.16 secs. The shear wave period is greater in the carotid compared to the radial artery, due to the carotid's larger diameter resulting in a slower period of oscillation of the pulse generated wake of high frequency shear waves.

The arterial mechanical behavior described to date, has concentrated on the small peripheral arteries; primarily the radial artery. For example, a 69 year old male mildly hypertensive, age related, with a resting BP of 124/75 mmHg was recorded over the left radial artery both before and after exercise as shown in FIG. 11. The anelastic model power law coefficients were $\beta_S$=0.67 and a $\beta_D$=0.4 at rest, and $\beta_S$=1.1 and a $\beta_D$=0.5 after exercise, for the left radial artery. Similar measurements were conducted on the subject's right carotid artery, with the at rest waveforms shown in FIG. 15A for a single cardiac cycle. The carotid anelastic power law coefficients were the same as the subject's radial artery, for both at rest and after exercise.

The suction wave due to the closure of the aortic valve is shown as 91. Note it is a forward traveling wave, positive dPdU, and being a suction wave results in decreasing the magnitude of both the pulse pressure waveform PPW and pulse velocity waveform PUW. The reflected wave due to the closure of the aortic valve is given by 92, and travels down the ascending aorta and abdominal aorta, reflected at the bifurcation and travels upwards to the carotid, as a forward suction wave. The wave denoted by 93 is a forward suction wave at the carotid, with its origin being the coronary artery, Davies et al. 2006, as the backward suction (decompression) wave in the coronary artery that is of clinical importance as the collapse and recovery of the coronary artery results in this backward suction (decompression) wave, which results in three times the blood flow in the coronary artery compared to its positive pressure dominant pushing wave during systole. This backward traveling suction wave in the coronary artery travels to the carotid as a forward suction wave. The volume and energy associated with this coronary artery has been extensively evaluated on numerous subjects, healthy, hypertensive and heart failure, using invasive techniques.

FIG. 15B denoted as 94 shows the normalized plot of PPW versus PUW over the carotid artery with the systolic (pressurizing) phase denoted as 95, and the diastolic (depressurizing) phase denoted as 96. The pulse excited wake of induced shear waves, 89 and 90, peak mid-systole and being highly dissipative, are virtually totally dissipated by systole. The plot of PPW versus PUW, denoted as 94, and the dPdU waveform 88 given in 86, both clearly show the carotid has no reflected waves. The forward traveling suction waves, 91, 92 and 93, during the diastolic phase yield the changes shown in 96, due to the unload/load nature of these suction waves. Both figures, FIG. 15B and FIG. 15A, clearly show that the carotid is void of reflected waves in healthy subjects. Due to the lack of reflected waves in the carotid compared to the radial artery, the PWV, i.e. $C_P$ needs to be determined by the placement of an additional sensor on the device for carotid artery monitoring, be it PPG, force or velocity to enable the carotid $C_P$ to be quantified.

Figures 16A, 16B, 16C:
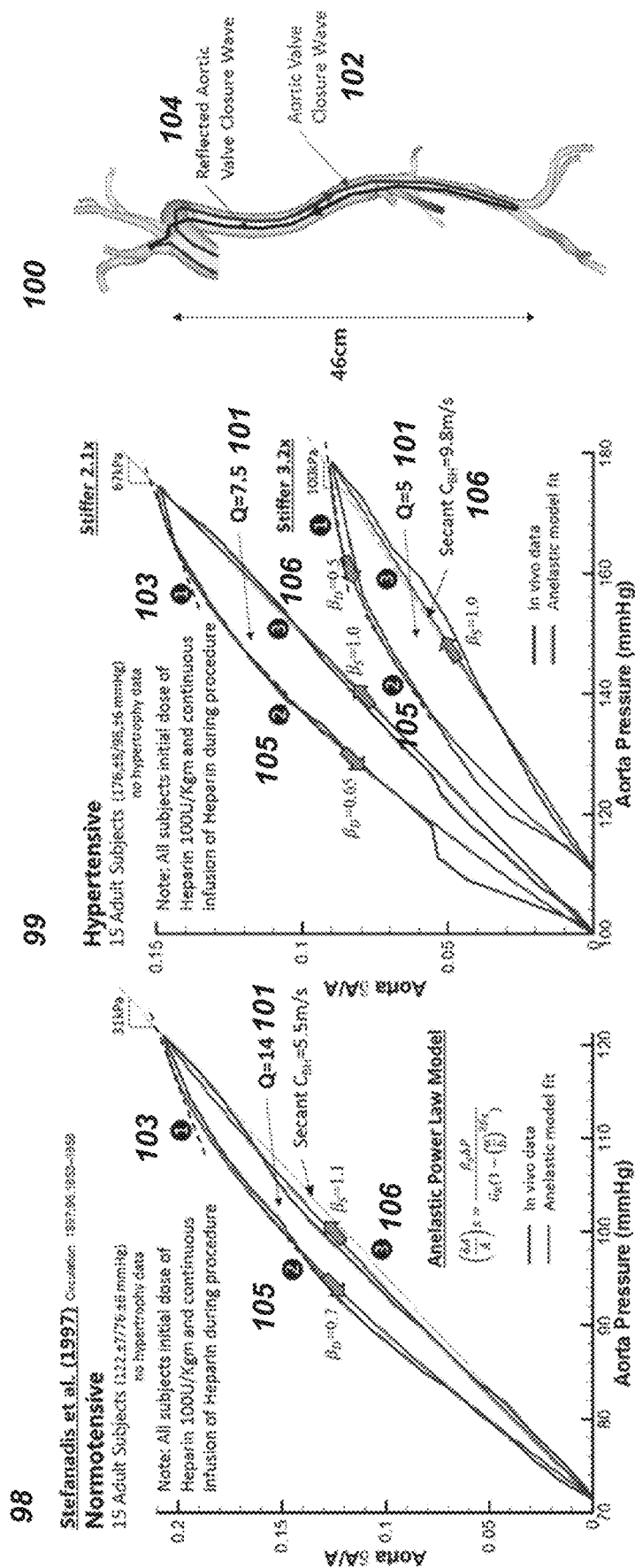
FIG. 16A is the descending aorta pressure versus area change for normotensive subjects.
FIG. 16B is the descending aorta pressure versus area change for hypertensive subjects.
FIG. 16C is a view showing the path lengths of the aortic valve closure wave and its bifurcation reflection.

In FIG. 16A and FIG. 16B denoted as 98 and 99, plots of aortic pressure versus aortic volume change of the descending aorta from 15 healthy and 15 hypertensive subjects, are shown collected from invasive catheter measurements, Stefanadis et al. 1997. The anelastic power law model is fitted to these plots with Quality factors, 101, ranging from 14 for the healthy subjects, to 7.5 and 5 for hypertensive subjects. The systolic $\beta_S$ power law coefficients change minimally from 1.1 to 1.0 for the healthy and hypertensive subjects respectively. The diastolic RD power law coefficients vary from 0.7 for the healthy subjects to 0.5 for the hypertensive subjects, with the secant modulus changing significantly from 31 kPa to 100 kPa. The aortic valve closure wave 91 travels up the ascending aorta, and down the descending aorta as shown in 100, FIG. 16C, and denoted as 102 for its travel path. This wave travels at a wave speed, shown by the slope of PPW versus PVW plots, denoted as 103. The reflected aorta valve closure wave, 104, is reflected from the bifurcation and travels back up the descending aorta to the carotid artery, at approximately half the wave speed of the aortic valve closure wave, 102. The differences in these two wave speeds is shown by the diastolic phase slopes of 103 and 105. The ratio of the time intervals of the zero ordinate of the waves 91 and 92 given in FIG. 15A for the wave intensity, dPdU, provides a measure of the Quality factor of the descending and abdominal aorta. The ratio of the slopes 105 and 103 enable the secant modulus, 106, to be determined from the time interval difference between the arrivals of the two waves, 91 and 92, at the carotid artery as shown in FIG. 15A.

In FIG. 15A, the suction wave from the aortic valve closure 91 has been reflected from the aortic bifurcation and arrives as a second forward traveling suction wave shown as 92 at a difference in the time abscissa values of 0.213 secs. That is, this time interval is the time for the aortic valve closure wave to travel from the aortic valve down to the aortic bifurcation, be reflected back, and travel upwards to the carotid artery; minus the time for the actual aortic valve closure wave to travel from the aortic valve to the carotid artery. From the anelastic power law model of the aorta, early to mid-diastole, for normotensive and hypertensive subjects, the downward traveling wave has a tangential wave speed of approximately twice the upward traveling wave's tangential wave speed, due to the differing pressures experienced by the respective upwards and downwards traveling waves. Knowing the distance from the suprasternal notch to the aortic bifurcation, 46 cm for this subject, enables the PWV to be determined for this path length. From the anelastic power law model, the aortic valve closure wave in the carotid travels at twice the wave speed of the reflected aortic valve closure wave in the carotid artery. The distance from the suprasternal notch to the carotid measuring point is 9 cm, and two measurement points in the carotid would yield the carotid PWV. The subject's aortic PWV is 6.7 m/s, which is equivalent to the secant aorta PWV for the applied pulse pressure (systole minus diastole). This path length entails the most important artery in the body, the aorta, and thus its PWV is of significant clinical interest, and a simple direct measurement of its PWV is extremely useful. From determining the F5/F1 ratio of the abdominal aorta as shown in FIG. 13, then the ratio of $C_L/C_{BH}$ is known and thus the secant $C_{BH}$ wave speed can be determined from equation 3. Therefore, the lumped secant $C_{BH}$ wave speed of the descending, thoracic and abdominal aorta of this subject is 5.3 m/s.

Figure 17B:
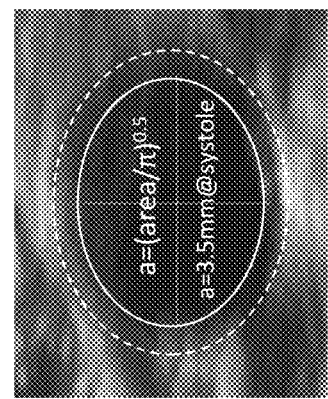
FIG. 17B is an ultrasound view near systole of the carotid artery inner radius for the calculation of the effective blood viscosity in vivo, arterial wall shear and shear rate.
Figure 17A:
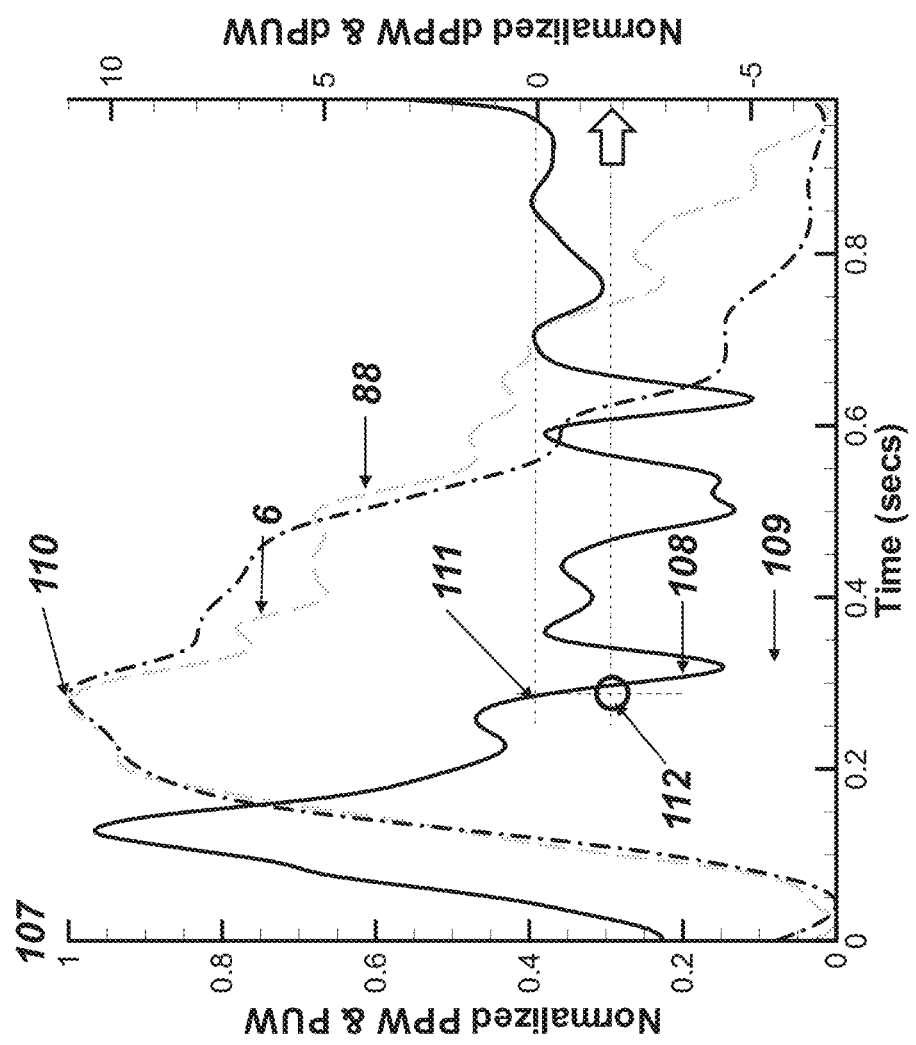
FIG. 17A is the time history of the normalized peripheral pulse pressure waveform (PPW) and velocity waveform (PUW), recorded from the force and velocity sensors positioned over the carotid artery, and the calculated first time derivatives of the PPW and PUW waveforms, for the calculation of the effective blood viscosity in vivo, arterial wall shear stress and shear rate.

FIG. 17A shows the time histories, 107, of the normalized PPW, PVW and PUW waveforms over the carotid artery for Subject C. The first time derivatives, dPPW and dPUW, of the waveforms PPW and PUW are shown in this figure denoted by 108 and 109. At systole, 110, the PPW and PUW waveforms are virtually in phase and coincident, as given by the enlarged view FIG. 17B. The respective values of dPPW and dPUW at the time valve of 110 are shown as 111 and 112, respectively, and shown in the enlarged view in FIG. 17C. The ordinate values at 111 and 112 for dPPW and dPUW are given in FIG. 17C. Note, the change in time derivatives, dPPW and dPUW, at and around systole are approximately linear, and both PPW and PUW are in phase during the systolic phase, as are dPPW and dPUW, with only minor differences due to the pulse excited shear waves, 89 and 90, shown in FIG. 15A.

$$\frac{\partial u_z}{\partial t} = -\frac{1}{\rho}\frac{\partial p}{\partial z} + \frac{\eta}{\rho r}\frac{\partial}{\partial r}\left(r\frac{\partial u_z}{\partial r}\right) \quad (4)$$

Pulsatile blood flow in a straight uniform diameter artery, distant from intersections, is given by the Navier-Stokes equations for fully developed flow given by equation 4. where $u_z$ is the velocity in the z (axial) direction, p is the density of blood, p is the pressure, $\eta$ is the apparent viscosity, and r is the radial direction. The relative importance of the pulsating forces (first term on the right hand side of equation 4) to the viscous resistance (second term on the right hand side of equation 4) in a given vessel is defined by the Womersley number ($\alpha$), $\alpha=a(\rho\omega/\eta)^{1/2}$, where a is the vessel inner radius, or its equivalent from the vessel's cross-sectional area, $\alpha=(area/\pi)^{1/2}$, $\omega$ is $2\pi f_{HR}$, where $f_{HR}$ is the beat frequency of the heart.

An approximate velocity profile model of the Navier-Stokes equations is utilized to provide a first-order approximation for the wall shear stress and the nonlinear term in the momentum equation, as a function of local flow and pressure gradient in the time domain. This time domain first-order approximation is modified to account for shear-thinning behavior in the boundary layer and simplified when the driving pressure gradient is zero. Knowing the inner radius of the vessel and an estimate of $\eta$ for the blood vessel, the value of Womersley $$\zeta_c = \left(\frac{a_c}{a}\right)^{\frac{1+n}{n}} \text{ and } \frac{a_c}{a} = \max\left[0, 1 - \frac{\sqrt{2}}{\alpha}\right] \quad (5)$$

number $\alpha$ is estimated, the frictional boundary layer thickness is determined from the below relationship for $$\frac{a_c}{a}$$

detailed in equation 5.
where $a_c$ is the radius of the central core, within which there is a flat velocity profile of $v_c$.

An estimate for the power-law flow behavior index is made based on the estimated shear rate, $\dot{\gamma}$. The determined whole blood viscosity is not sensitive to the n value estimated, provided it is a reasonable estimate for the respective shear rate range. The proposed range of n with $\dot{\gamma}$ is; $\dot{\gamma}>50/s$ n=0.85, $\dot{\gamma}<5/s$ n=0.35, and $\dot{\gamma}$ between 5/s and 50/s, n=0.6. At zero driving pressure gradient, $\partial P/\partial t=0$, the time derivative of the normalized velocity waveform, the mean axial normalized velocity and inner radius of the blood vessel, the whole blood viscosity can be determined from equation 6, with the mean axial velocity and wall shear stress at zero driving pressure gradient are given by equations 7 and 8.

$$\frac{\partial v_z}{\partial t} = \frac{2\eta(1+n)}{\rho n a^2 (1-\zeta_c)} \bar{v}_z \quad (6)$$

$$\bar{v}_z = \frac{\left(\frac{a_c}{a} - 1\right)}{\ln\left(\frac{a_c}{a}\right)} v_c \quad (7)$$

$$\tau_{rz}|_{r=a} = \eta\left(\frac{\partial v_z}{\partial r}\right)\bigg|_{r=a} = \frac{-\eta(1+n)}{na(1-\zeta_c)} \bar{v}_z \quad (8)$$

From the normalized pressure and velocity blood vessel waveforms, the time derivative of $v_z$ is determined at zero driving pressure gradient. The blood vessel inner radius needs to be known at the pulse pressure the time derivative of $v_z$ was selected. The whole blood viscosity, $\eta$, is determined directly from equation (6), and the shear rate, $\dot{\gamma}$, is given by equation (8), knowing the blood flow velocity in an artery from the arterial blood pulse pressure and secant PWV; while, in a vein doppler ultrasound can be used.

FIG. 17A the whole blood viscosity point of measurement, when the driving pressure gradient is zero 111, is highlighted by the circle symbol 112, and the inner carotid radius of 3.5 mm as shown in FIG. 17B. The time derivative of the normalized $v_z$ is 1.7 at the maximum systolic pulse pressure, and from equation (6), the 71 yr mildly hypertensive male's whole blood viscosity (Subject B) η=2.5 cP. The blood velocity in the central core of the carotid artery at maximum systolic pulse pressure is given by $\Delta P/(\rho C^S_P)$, and for the 71 yr mildly hypertensive male was 67 cm/s, with a mean maximum systolic blood velocity of 59 cm/s from equation (7). The maximum systolic shear rate in the carotid artery is 850/s, as given by equation (8).

FIG. 18A depicts the time histories 113 of the waveforms PPW 6, PVW 7, and PUW 88 over a single cardiac cycle measured over the carotid artery by the disclosed processing device 3, shown in FIG. 18B as 114 over placement over the carotid artery, with sensors 5 connected to the device 3, shown in top view 114 and underside view 115. For the carotid artery, the device is mounted on a flexible adhesive fabric 116. The aortic valve is shown in the open position 117 in FIG. 18C and the closed position 118 in FIG. 18D, with aortic walls denoted by 117. The waveforms collected by the device, as shown in FIG. 18a were shown earlier in FIG. 15A, with the wave intensity analysis waveform dPdU calculated from the waveforms PPW and PUW shown as 89. The suction wave due to the closure of the aortic valve is shown as 91. Note it is a forward traveling wave, positive dPdU, and being a suction wave results in decreasing the magnitude of both the pulse pressure PPW and pulse velocity PUW. Subtracting the Windkessel flow waveform from systole to diastole from the PUW waveform yields the diastolic waveform designated as PWU (pulse wavelet velocity) and denoted as 120. Integrating the waveform PUW over the time abscissa values from the start of the cardiac cycle to systole, yields the normalized left ventricle ejected volume (LVEV) 121. Integrating the change in the waveform PWU, 120, over the time interval of closure of the aortic valve, yields the aortic valve closure volume (AVCV) as given by 122. The subject does not have any observed aortic valve regurgitation volume (AVRV), which would be apparent by a change in the wavelet shape of 92, generally involving a second peak. If such regurgitation is present, it's normalized volume can be determined by integrating the PWU waveform over its respective time abscissa taking into account that the regurgitation occurs during the aortic valve closure and that modified PWU waveforms need to be generated to correctly calculate the normalized AVCV and AVRV. Integrating PWU over the rebound period of the aortic valve closure, yields the volume denoted as 123, being the aortic valve rebound volume (AVBV), which is a measure of the compliance of the aortic valve and its wall compliance. Integrating the PWU waveform over the time interval of the coronary artery suction wave as shown, yields the coronary suction wave volume (CSWV) as denoted by 124. The ratio of the two normalized volumes (121/122) for this subject is 37.4 for the cardiac cycle shown. That is the heart's ejected left ventricle volume is 37.4 times the closure volume of the aortic valve. If there are no earlier reflected waves from the aortic valve closure wave 91, then the normalized volume of its reflected wave 92 would be the same as 122. The Q (Quality factor) of this subject's aorta (from the descending aorta to the aorta bifurcation) is the inverse of 1.0 minus the ratio of the time abscissa values of the waves 91 and 92 being 0.063/0.069 for an aorta Quality factor of 11. Any abnormalities (stiffening, plaque buildup, arteriosclerosis, aneurysm or dissection) in the ascending aorta will be apparent from changes in the PPW and PUW during systole and aortic valve closure. Similarly, abnormalities in the descending, thoracic or abdominal aorta will give rise to additional earlier reflected waves before the arrival of the bifurcation reflected aortic valve closure wave, and changes in the PPW and PUW waveforms in the reflected aortic valve closure wave. Location of these abnormalities can be determined from the arrival times of any such additional reflected waves.

The aortic valve is shown in the open position 117 in FIG. 18C and the closed position 118 in FIG. 18D. The cross-sectional area of the aortic valve is typically ~2 cm$^2$/m$^2$ of a subject's body surface area (BSA). For this subject's weight and height, his BSA=2 m$^2$, for an aortic valve total cross-sectional area of 4 cm$^2$. The open cross-sectional area of a normal aortic valve of this size is 2.6 cm$^2$, for a closure volume (fully open to fully closed) of 2.358 cm$^3$. The stroke volume of this subject over the cardiac cycle shown in FIG. 18A is 37.4 times 2.35 cm$^3$ being 88 mL. The subject's heartbeat period for this cardiac cycle is 0.93 secs, i.e. a heart rate of 65 bpm. The cardiac output (CO) is the stroke volume times the heart rate being 5.7 L/min, with the cardiac index (CI=CO/BSA) of 2.9 L/min/m$^2$. The coronary artery suction wave as observed at the carotid artery has a normalized volume ratio with respect to the aortic valve closure volume, i.e. volume 124 divided by 122, is ~30%, which is typical of an older healthy male. The left ventricle ejected volume, the aortic valve closure volume and the coronary artery suction wave volume can thus be determined over each cardiac cycle, and their variability displayed as well as their respective time periods. Such variations can quantify valve impulse closure, valve regurgitation, valve compliance and valve conformance for either natural, repaired or artificial heart valves under normal at rest conditions or during differing cardiac stress conditions, plus also quantification of coronary artery flow behavior and performance as depicted by its dominant backward traveling suction wave, such as during exercise stress tests or during simple maneuvers, e.g. the Valsalva or the modified Mueller maneuver.

In FIG. 19A are the time histories 125 of the PPW, PVW and PUW waveforms for the same subject as shown earlier in FIG. 18A. The device 3 placed over the carotid artery is given in FIG. 19B. The open and closed positions of the aortic valve are shown in FIGS. 19C and 19D. In FIG. 18A the normalized volumes of LVEV, AVCV, etc. were calculated from the PUW waveform. In FIG. 19A the normalized energies associated with normalized volumes are determined. The normalized volumes are very useful on their own, but are even more important when they are associated with their respective normalized energies, which are calculated as described. In FIG. 19A, the carotid pulse power waveform, denoted as PKW, is calculated from the PPW and PUW waveforms, and is shown as 126. The diastolic portion of PKW is modified to remove the Windkessel flow power waveform, producing the diastolic pulse power wavelet waveform, designated as PWK, and shown as 127. The energy associated with the left ventricle ejected volume is given by the integration of PKW as shown by 128. The energy associated with the aortic valve closure is shown as 129, the energy associated with the aortic rebound as 130 and the coronary artery suction wave energy as 131. The ratio of the two normalized volumes (127/128) for this subject is virtually the same as the normalized volume ratio detailed in FIG. 19A. That is the heart's ejected left ventricle volume and power is 37.4 times the closure volume and power, respectively, of the aortic valve. The subject does not have any observed aortic valve regurgitation volume (AVRV), which would be apparent by a change in the wavelet shape of 92, generally involving a second peak. If such regurgitation is present, it's normalized energy can be determined by integrating the PWK waveform over its respective time abscissa taking into account that the regurgitation occurs during the aortic valve closure and that modified PWK waveforms need to be generated to correctly calculate the energies associated with both aortic valve closure and regurgitation. Rather than take the time increment ratio of the aortic valve closure wave to its reflected wave as a measure of the descending and abdominal aorta Quality factor, as shown in FIG. 18A, the energy associated with the reflected aortic valve closure wave 92 can be integrated from the PWK waveform as shown by 132. The ratio of 132 to 129 is 0.9, thus the descending, thoracic and abdominal aorta have a lumped Quality factor of 10. Any abnormalities (stiffening, plaque buildup, arteriosclerosis, aneurysm or dissection) in the ascending aorta will be apparent from changes in the PPW and PUW during systole and aortic valve closure. Similarly, abnormalities in the descending, thoracic or abdominal aorta will give rise to additional earlier reflected waves before the arrival of the bifurcation reflected aortic valve closure wave, and changes in the PPW and PUW waveforms in the reflected aortic valve closure wave. Location of these abnormalities can be determined from the arrival times of such additional reflected waves.

Figure 20B:
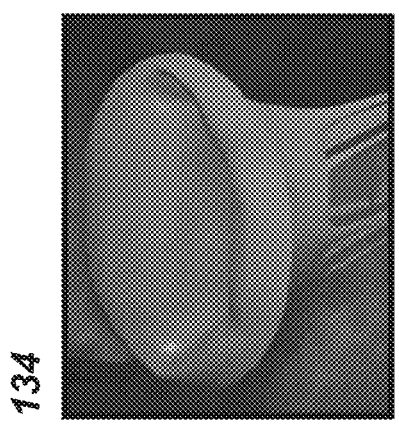
FIG. 20B shows the mitral valve in an open position.
Figure 20C:
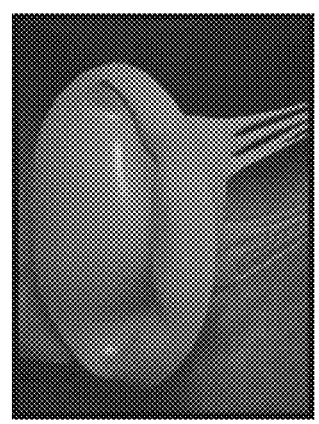
FIG. 20C shows the mitral valve in a closed position.
Figure 20A:
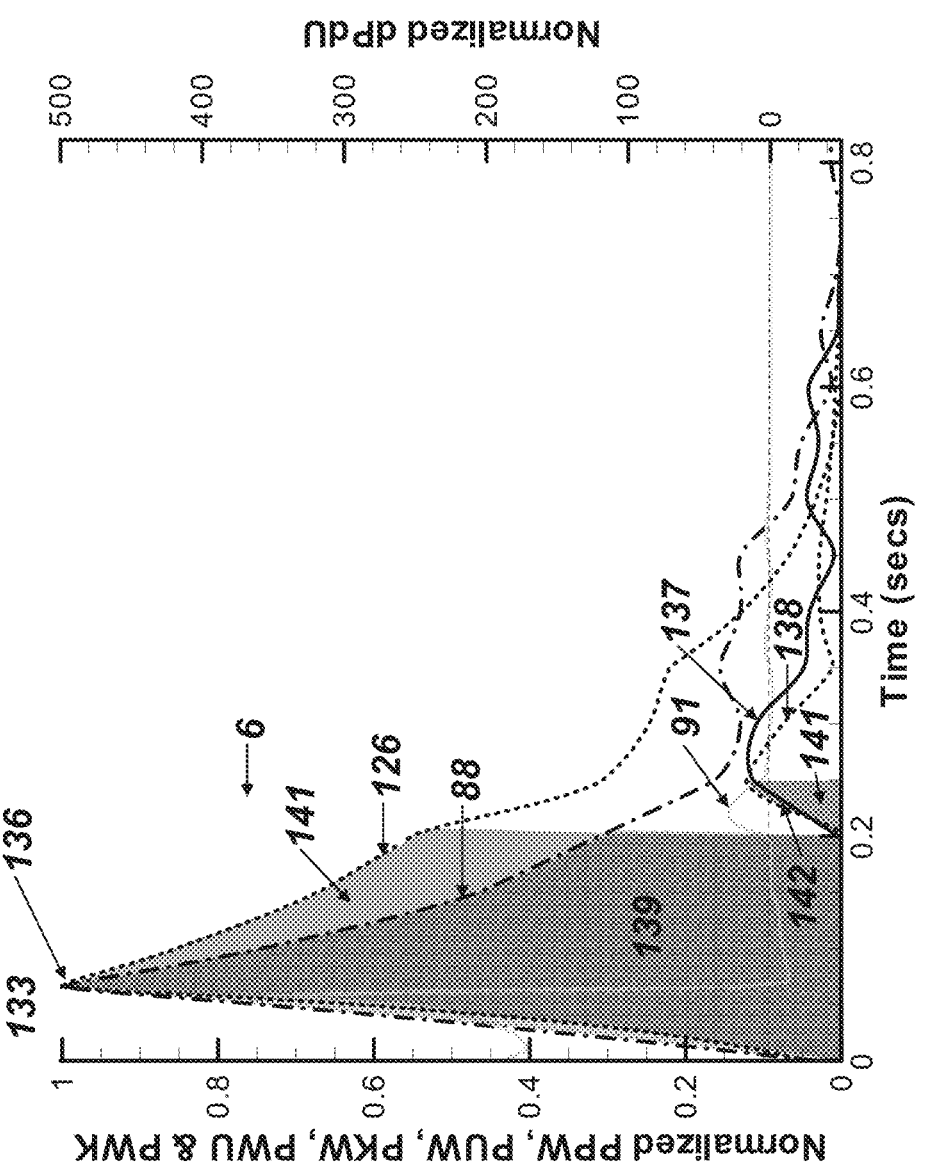
FIG. 20A is the time history of the peripheral pulse pressure waveform (PPW) and velocity waveform (PUW), recorded from invasive monitoring of the carotid artery of a subject experiencing severe mitral valve regurgitation, with the calculated wave intensity analysis (dPdU) waveform and the calculated pulse power waveform (PKW), both constructed from the PPW and PUW waveforms.

In FIG. 20A are the time histories 133 over the carotid artery of the PPW (6), PUW (88) and PKW (126) waveforms for a subject experiencing severe mitral valve regurgitation, determined by invasive catheter measurements, after Nikki et al., 1999. The PPW waveform is not from pressure measurements, but was in fact the diametral change of the carotid artery, which is a close linear fit to the pulse pressure waveform for the carotid artery for the majority of the systolic phase, but in error during the diastolic phase. The carotid arterial diametral time histories were modified to better reflect pulse pressure, and are shown as the PPW, denoted as 6. The actual blood pressures were measured over the brachial artery and are thus in error for the carotid, and thus only normalized waveforms are shown. Brachial BP was 100/64 mmHg. The blood velocity at systole was approximately 80% of similar aged healthy subjects, who showed no signs of mitral valve regurgitation. The LVEV for the patient is therefore significantly lower than similar aged healthy subjects. The wave intensity is shown as 89 and the aortic valve closure wave denoted by 91. The open and closed positions of the mitral valve are shown as 134 in FIG. 20B for the open position, and as 135 for the closed position in FIG. 20C. In FIG. 20A, the PUW 88 and PKW 126 waveforms drops off significantly at 136, in striking contrast to a subject with no mitral valve regurgitation, see FIG. 19A. The wavelet for the aortic valve closure wave is barely discemable in the wave intensity, shown as 91. The pulse wavelet velocity (PWU) for the diastolic phase is shown as 137, being the PUW waveform minus the Windkessel flow waveform. The pulse wavelet power (PWK) for the diastolic phase is shown as 138, being the PKW waveform minus the Windkessel power waveform. The time integration of PUW up to systole, being the LVEV, is shown as 139. The integration of PUW over the aortic valve closure, being the observed AVCV, is shown as 140. The time integration of the PKW waveform up to systole is shown as 141. The ratio of the normalized volumes (139/140) is ~33, while the ratio of the normalized energies (141/142) is ~47, a significant difference from those shown for a subject with no mitral valve regurgitation, in which the ratios of normalized volumes and energies were similar. The significant differences in the waveforms, normalized volumes and energies of a patient with severe mitral valve regurgitation 133 compared to those of healthy subjects 125, enable a detailed assessment of mitral valve performance to be quantified from the non-invasive measurements of carotid waveforms using the device 3, shown in FIG. 19A over the carotid artery. Any repair or replacement of the mitral valve can also be assessed for its performance and compliance from such non-invasive measurements over the carotid artery using the device 3. The carotid artery waveforms from the device 3, provide actual magnitudes of pulse pressure and velocity over each cardiac cycle as has been described earlier. Therefore, it is possible from these non-invasive waveforms to quantify the subject's heart and heart valves performances, either in their original state, surgically repaired or catheter replaced.

The disclosed devices and methods can be used to determine the health status of a subject, more specifically the cardiovascular health status of an individual. In vivo quantification of anelastic changes in arterial blood vessels is essential in diagnosing the issues relating to aging and disease, plus determining the impact of medication on changes to the peripheral arterial blood vessels' anelastic properties and their hypertrophy. Arterial hypertrophy refers to the abnormal enlargement or thickening of the walls of arterial blood vessels. This leads to a narrowing of the vascular lumen. Prolonged hypertrophy without intervention can lead to reduced blood supply to the heart, irregular heartbeat, and alterations in blood pressure. The disclosed devices and methods can be used to determine the hypertrophic status of a subject.

Hypertension is often cited as an early cause of hypertrophy. The hypertensive state of a subject can be correlated to age, and as such are related to the effects of aging, or whether the hypertensive state is being accelerated due to the impacts of disease, life style or medication on the respective subject, can be assessed.

Rapid decline in blood pressure or stroke volume can warn of low blood volume (hypovolemia), hypotension perfusion and the imminent risk of the subject entering shock conditions. The disclosed device and methods of use thereof can be used to constantly monitor a subject diagnosed with or suspected of having pneumonia, cardiac disorders, sepsis, asthma, obstructive sleep apnea, hypopnea, anesthesia, pain, or narcotic use. Low stroke volume can indicate onset of endothelium dysfunction (capillary leak syndrome), myocardial dysfunction, hypotension perfusion, respiratory distress or hypoventilation in the subject. In one embodiment, the disclosed devices and methods can be used to monitor mechanical anelastic in vivo properties of the arterial blood vessels, blood pressures, stroke volume, cardiac output, blood viscosity, performance of the heart valves and vascular tone of the subject in real-time in order to alert a physician or caretaker to sudden changes in the subject's health status.

The calculated changes in the arterial blood vessel hemodynamic and anelastic properties can be used to quantify the extent of vasodilation, vasocontraction, loss of stroke volume, change in blood viscosity, induced hypertension/hypotension and possible onset of cardiogenic shock. The determination of the anelastic blood vessel properties provides a direct measure of whether exercise or medication induced vasodilation is sufficient in improving the tone of the subject's peripheral artery blood vessels, and thus reverse or slow the rate of change of the subject's hypertensive state.

The disclosed methods can be used to record the subject's hemodynamic properties and arterial blood vessel anelastic properties over time. The historical recoding can enable a physician or caretaker to more accurately determine the impact of current procedures, any prescribed medication, diet or exercise program, stress, or other lifestyle changes on the subject's cardiovascular state.

The non-invasive, real-time measurements and calculations of the disclosed method can be used to diagnose cardiovascular diseases and disorders. Changes in cardiac output, blood viscosity, heart valve closure and regurgitation volumes and energies, blood pressure, or intravascular volume status from a predetermined healthy subject baseline can be indicative of disease. Exemplary cardiovascular diseases and disorders include but are not limited to hypertension, hyperlipidemia, coronary heart disease, atherosclerosis, congestive heart failure, peripheral vascular disease, myocardial infarction, myocardial dysfunction, cardiogenic shock, angina, heart failure, aortic stenosis and aortic dissection.

The disclosed methods can also be used to monitor a subject's response to a treatment for cardiovascular disease. In such an embodiment, measurements are calculated before the subject is administered the treatment to establish a baseline for that subject. Measurements are then calculated throughout treatment. In one embodiment, an unchanged measurement can indicate that the physician should change the treatment type or the amount of treatment that is being administered. Alternatively, if the subject's measurements change to the healthy subject baseline levels, the treatment could be discontinued or tapered down.

Exemplary treatments for cardiovascular diseases and conditions include but are not limited to ACE inhibitors, such as Lisinopril, and benazepril; diuretics, such as hydrochlorothiazide, triamterene, chlorothiazide, and chlorthalidone; beta blockers, such as atenolol, metoprolol, nadalol, labetalol, bisoprolol, and carvedilol; antihypertensive drugs such as losartan and valsartan; calcium channel blockers, such as amlodipine and nifedipine; vasodilators, such as hydralazine; hyperlipidemia medications such as atorvastatin, fluvastatin, lovastatin, pitavastatin, pravastatin, rosuvastatin, and simvastatin; thrombolytic agents such as anistreplase, reteplase, streptokinase, and kabikinase; antiplatelet drugs such as aspirin, clopidogrel, prasugrel, ticagrelor, ticlopidine, dipyridamole, cilostazol, abciximab, eptifibatide, and tirofiban; nitrates; anticoagulants; such as heparin, warfarin, rivaroxaban, dabigatran, apixaban, adoxaban, enoxaparin, and fondaparinux.

In one embodiment, the disclosed methods can indicate that the subject is entering a stage of change in aortic valve closure volume, closure time, or valve regurgitation, that may indicate a possible onset of myocardial dysfunction.

The disclosed methods can also indicate that the subject is entering a stage of change in aorta PWV due to a possibly lower mean blood pressure, acute decline of recirculating blood volume, that may indicate a possible onset of cardiogenic shock or myocardial dysfunction or an elevated risk of an aortic aneurysm or dissection.

Finally, it will be understood that the preferred embodiment has been disclosed by way of example, and that other modifications may occur to those skilled in the art without departing from the scope and spirit of the appended claims.

OTHER PUBLICATIONS

Davies J E, Whinnett Z I, Francis D P, et al. Evidence of a Dominant Backward-Propagating "Suction" Wave responsible for Diastolic Coronary filling in Humans, attenuated in Left Ventricular Hypertrophy. Circulation 2006; 11,113(14):1768-78.

Laurent S, Girerd X, Mourad J, et al. Elastic Modulus of the Radial Artery Wall Material is not increased in Subjects with essential Hypertension. Arteriosclerosis and Thrombosis 1994:14,7.

Millasseau S C, Guigui F G, Kelly R P, et al. Noninvasive Assessment of the Digital Volume Pulse: Comparison with the Peripheral Pressure Pulse. Hypertension 2000; 36; 952-956.

Niki K, Sugawaral M, Uchida K, et al. A Noninvasive Method of measuring Wave Intensity, a new Hemodynamic Index: Application to the Carotid Artery in Patients with Mitral Regurgitation before and after Surgery. Heart Vessels 1999; 14; 263-271.

Stefanadis C, Dernellis J, Vlachopoulos C, et al. Aortic Function in Arterial Hypertension Determined by Pressure-Diameter Relation, Effects of Diltiazem. Circulation, 1997; 96:1853-1858.

What is claimed is:

1. A method of quantifying hemodynamic parameters and mechanical anelastic in vivo properties of an arterial blood vessel of a subject in near real time, the method comprising the steps of:
    a. obtaining a pulse arterial pressure waveform (PPW), a pulse arterial volume waveform (PVW) and a pulse arterial velocity waveform (PUW) from the arterial blood vessel in the subject over a cardiac cycle;
    b. calculating a time phase shift between the PPW and the PVW, blood pressure, and power law components of an anelastic model from the waveform PPW, waveform PVW, blood viscosity, cardiac output, performance of heart valves from the waveform PPW and waveform PUW; and
    c. determining the mechanical anelastic in vivo properties of the arterial blood vessel, blood pressure, stroke volume, cardiac output, blood viscosity, performance of aorta and mitral heart valves, and vascular tone of the subject based upon the calculations.

2. The method of claim 1, wherein the waveform PPW and waveform PVW are obtained by placing a device comprising a pulse optical plethysmograph sensor, a force sensor, and a strap tension actuator over the arterial blood vessel.

3. The method of claim 1, wherein the arterial blood vessel is a radial artery.

4. The method of claim 2, wherein the pulse optical plethysmograph sensor is selected from the group consisting of an infra-red optical plethysmograph sensor, a visible light optical plethysmograph sensor, and a pulse oximetry sensor.

5. The method of claim 2, wherein the force sensor is a strain gauge selected from the group consisting of a piezoelectric strain gauge, a capacitance strain gauge, and a mems strain gauge.

6. The method of claim 2, wherein the strap tension actuator is selected from the group consisting of an electrical tension actuator, a hydraulic tension actuator, a pneumatic tension actuator, a mechanical tension actuator, and a manually tension actuator.

7. The method of claim 1, wherein the waveform PPW and waveform PVW are obtained from the arterial blood vessel at systole and diastole by applying a normal pressure to the arterial blood vessel in an amount effective to flatten the arterial blood vessel.

8. The method of claim 6, wherein the subject's pulse pressure is assessed over each cardiac cycle from a single strap tension.

9. The method of claim 1, wherein the strap tension actuator for each subject is only activated once per two months.

10. The method of claim 1, wherein the subject's level of hypertrophy is calculated from the subject's in vivo anelastic power law coefficients.

11. The method of claim 1, wherein the change of the in vivo anelastic power law coefficients determine the extent of vasodilation or vasocontraction experienced by the subject.

12. The method of claim 1, wherein the blood viscosity is determined at or close to systole from the waveform PPW and waveform PUW.

13. A method of quantifying hemodynamic parameters of a subject in near real time, the method comprising the steps of:
   a. placing a device comprising a pulse optical plethysmograph sensor, a force sensor, a velocity sensor, and a pressure actuator over a subject's artery;
   b. obtaining a pulse arterial pressure waveform (PPW), a pulse arterial volume waveform (PVW), and a pulse arterial velocity waveform (PUW) from the device over a cardiac cycle;
   c. determining blood pressure and power law components of an anelastic model from the waveform PPW and waveform PVW, and a cardiac output from the waveform PPW and waveform PUW;
   d. displaying the blood pressure, stroke volume, cardiac output, blood viscosity, performance of heart valves, and vascular tone of the subject.

14. The method of claim 13, wherein obtaining the waveform PPW, waveform PVW, and waveform PUW over the cardiac cycle comprises activating a strap tension actuator to modify normal pressure acting on the artery.

15. The method of claim 13, wherein the velocity sensor is selected from the group consisting of a Hall sensor, an ultrasound doppler sensor, and a mems sensor, with the Hall sensor having an applied magnetic field from a magnet.

16. The method of claim 13, wherein the displaying step further comprises displaying information selected from the group consisting of an alert message, a signal generated at critical states of the subject's blood pressure, stroke volume, cardiac output, blood viscosity, performance of the heart valves, and vascular tone.

17. The method of claim 13, wherein the blood pressure, stroke volume, cardiac output, blood viscosity, performance of the heart valves, and vascular tone of the subject are continuously calculated and displayed.

18. The method of claim 13, further comprising intravenously administering a fluid to the subject and calculating and displaying the blood pressure, stroke volume, cardiac output, blood viscosity, performance of the heart valves, and vascular tone of the subject after administration of the fluid.

19. The method of claim 18, further comprising adjusting the flow rate of the fluid that is administered intravenously to the subject based on the blood pressure, stroke volume, cardiac output, blood viscosity, performance of the heart valves, and vascular tone.

20. The method of claim 13, further comprising diagnosing the subject with disease if the blood pressure, stroke volume, cardiac output, blood viscosity, performance of the heart valves, and vascular tone of the subject deviate from a baseline established for a healthy individual.

21. The method of claim 20, further comprising administering a treatment to the subject.

22. A method of diagnosing and treating a cardiovascular disease or condition in a subject in need thereof, comprising:
   a. obtaining a pulse arterial pressure waveform (PPW), a pulse arterial volume waveform (PVW), and a pulse arterial velocity waveform (PUW) from an artery in the subject over a cardiac cycle;
   b. calculating arterial in vivo anelastic power law coefficients and secant modulus;
   c. determining blood pressure and power law components of an anelastic model from the waveform PPW and waveform PVW, cardiac output from the waveform PPW and waveform PUW, and a quality factor of a descending aorta based upon the calculations;
   d. diagnosing the subject with a cardiovascular disease if values calculated for the blood pressure, cardiac output, blood viscosity, performance of the heart valves, and the quality factor of a descending aorta deviate from a baseline established for a healthy individual;
   e. administering a treatment to the subject of a type and amount effective to reduce the symptoms of the cardiovascular disease or condition.

23. The method of claim 22, further comprising repeating steps (a)-(c) of claim 22 after administration of the treatment.

24. The method of claim 22, wherein the cardiovascular disease or condition has increased or decreased cardiac output, increased or decreased blood pressure, or increased or decreased intravascular volume status, or increased or decreased blood viscosity, or increased or decreased closure and/or regurgitation volumes and energies of the heart valves.

25. The method of claim 22, wherein the cardiovascular disease or condition is selected from the group consisting of hypertension, hyperlipidemia, coronary heart disease, atherosclerosis, congestive heart failure, peripheral vascular disease, myocardial infarction, myocardial dysfunction, cardiogenic shock, and aortic dissection.

26. The method of claim 22, wherein the treatment is selected from the group consisting of ACE inhibitors, beta blockers, diuretics, antihypertensive drugs, calcium channel blockers, hyperlipidemia drugs, vasodilators, thrombolytic agents, antiplatelet drugs, and anticoagulants.

27. The method of claim 22, wherein the method is used to diagnose diseases or conditions selected from the group consisting of respiratory distress, myocardial dysfunction, and hypoventilation in the subject.

28. The method of claim 22, wherein the waveform PPW, waveform PVW, and waveform PUW are obtained by a device selected from the group consisting of a pulse optical plethysmograph sensor, a force sensor, a velocity sensor, and a strap tension actuator.

29. The method of claim 28, wherein the sensors are positioned proximately to a peripheral artery, and wherein the waveform PPW, waveform PVW, and waveform PUW, originate from the peripheral artery.

30. The method of claim 22, wherein the subject's blood pressure is determined from waveform PVW systolic and diastolic minima and maxima points to determine systolic and diastolic pressures from the waveform PPW.

31. The method of claim 22, wherein the anelastic power law coefficients and quality factor are determined from normalized plots of waveform PVW versus waveform PPW.

* * * * *